United States Patent
Widmann et al.

(10) Patent No.: US 8,110,544 B2
(45) Date of Patent: Feb. 7, 2012

(54) RASGAP DERIVED PEPTIDE FOR SELECTIVELY KILLING CANCER CELLS

(75) Inventors: Christian Widmann, Lausanne (CH); Jiang-Yang Yang, Lausanne (CH); David Michod, Lausanne (CH)

(73) Assignee: Universite de Lausanne, Lausanne (CH)

( * ) Notice: Subject to any disclaimer, the term of this patent is extended or adjusted under 35 U.S.C. 154(b) by 1076 days.

(21) Appl. No.: 10/563,536

(22) PCT Filed: Jun. 30, 2004

(86) PCT No.: PCT/IB2004/002165
§ 371 (c)(1),
(2), (4) Date: Jun. 16, 2006

(87) PCT Pub. No.: WO2005/000887
PCT Pub. Date: Jan. 6, 2005

(65) Prior Publication Data
US 2006/0234929 A1  Oct. 19, 2006

Related U.S. Application Data

(60) Provisional application No. 60/483,691, filed on Jun. 30, 2003.

(51) Int. Cl.
*C07K 14/00* (2006.01)
*A61K 38/00* (2006.01)
(52) U.S. Cl. .............. 514/2; 514/12; 530/300; 530/350; 435/69.1; 536/23.5; 424/9.1
(58) Field of Classification Search .............. 514/2, 12; 530/300, 350; 435/69.1; 536/23.5; 424/9.1
See application file for complete search history.

(56) References Cited

U.S. PATENT DOCUMENTS

| | | | |
|---|---|---|---|
| 6,180,362 B1 | 1/2001 | Duchesne et al. | |
| 7,001,980 B1 | 2/2006 | Parker et al. | |
| 2006/0234929 A1 * | 10/2006 | Widmann et al. | 514/12 |

FOREIGN PATENT DOCUMENTS

| | | |
|---|---|---|
| WO | WO-94/03597 A1 | 2/1994 |
| WO | WO-99/65947 A2 | 12/1999 |
| WO | WO-03/018630 A1 | 3/2003 |

OTHER PUBLICATIONS

Yang et al., Mol. And Cell. Biology 21, 5346-5358 (2001).*
Duchesne, M. et al., "Identification of the SH3 domain of GAP as an essential sequence for Ras__GAP-mediated signaling," *Science*, vol. 259:525-528 (1993).
LeBlanc, Veronique et al., "Ras-GTPase activating protein inhibition specifically induces apoptosis of tumour cells," *Oncogene*, vol. 18(34):4884-4889 (1999).
Schwarze, S. et al., "In vivo protein transduction: delivery of a biologically active protein into the mouse," *Science*, vol. 285(5433):1569-1572 (1999).
Yang, Jiang-Yang et al., "Antiapoptotic Signaling Generated by Caspase-Induced Cleavage of RasGAP," *Molecular and Cellular Biology*, vol. 21(16):5346-5358 (2001).
Futaki, Shiroh et al., "Membrane permeability commonly shared among arginine-rich peptides," *Journal of Molecular Recognition*, vol. 16:260-264 (2003).
Osterman-Golkar, S. et al., "Evaluation of Genetic Risks of Alkylating Agents. II. Haemoglobin as a Dose Monitor," *Mutation Research*, vol. 34:1-10 (1976).
Roos, Wynand P. et al., "DNA damage-induced cell death by apoptosis," *Trends in Molecular Medicine*, vol. 12(9):440-450 (2006).
Feldmann, Pascale et al, "Control of Growth and Differentiation by Drosophila RasGAP, a Homolog of p120 Ras-GTPase-Activating Protein," *Molecular and Cellular Biology*, vol. 19(3):1928-1937 (1999).
Prendergast, George C. et al, "Ras Regulatory Interactions: Novel Targets for Anti-cancer Intervention?" *Bioessays*, vol. 16(3):187-191 (1994).
Widmann, Christian et al, "Mitogen-Activated Protein Kinase: Conservation of a Three-Kinase Module From Yeast to Human," *Physiological Reviews*, vol. 79(1):143-180 (1999).
Widmann, Christian et al, "Caspase-dependent Cleavage of Signaling Proteins during Apoptosis," *The Journal of Biological Chemistry*, vol. 273(12):7141-7147 (1998).
Yang, Jian-Yan et al, "A subset of caspase substrates functions as the Jekyll and Hyde of apoptosis," *European Cytokine Network*, vol. 13(4):404-406, (Dec. 2002).
Yang, Jian-Yan et al, "The RasGAP N-terminal Fragment Generated by Caspase Cleavage Protects Cells in a Ras/PI3K/Akt-dependent Manner That Does Not Rely on NFκB Activation," *The Journal of Biological Chemistry*, vol. 277(17):14641-14646 (2002).
Michod, David et al., "Effect of RasGAP N2 Fragment-Derived Peptide on Tumor Growth in Mice," *J. Natl. Cancer Inst*, vol. 101(11):828-832 (2009).

* cited by examiner

*Primary Examiner* — Chih-Min Kam
(74) *Attorney, Agent, or Firm* — Nelson Mullins Riley & Scarborough LLP; Debra J. Milasincic, Esq.

(57) ABSTRACT

The present invention relates to a peptide consisting in the N2 sequence of the RasGAP protein, a fragment thereof, or a variant thereof which enhances the ability of a drug to selectively kill cells. Furthermore, it relates to a pharmaceutical composition comprising as an active substance a pharmaceutically effective amount of the peptide.

55 Claims, 8 Drawing Sheets

B

HeLa

U2OS

MCF-7

H-Meso1

RASGAP DERIVED PEPTIDE FOR SELECTIVELY KILLING CANCER CELLS

RELATED APPLICATIONS

This application is a 35 U.S.C. §371 filing of International Application Number PCT/IB2004/002165 which was filed Jun. 30, 2004, which claims priority to U.S. Provisional Application No. 60/483,691, filed on Jun. 30, 2003. The contents of the aforementioned applications are hereby incorporated herein by reference.

FIELD OF THE INVENTION

The present invention relates to a peptide which enhances the ability of a drug to kill cells selectively in cancer cells. Furthermore, it relates to a pharmaceutical composition comprising as an active substance a pharmaceutically effective amount of at least one of said peptide.

BACKGROUND OF THE INVENTION

Tumors are diverse and heterogeneous, but all share the ability to proliferate without control. Deregulated cell proliferation coupled with suppressed apoptotic sensitivity constitutes a minimal requirement upon which tumor evolution occurs.

Apoptosis is the process by which cells enter programmed cell death, a vital phenomenon that takes place during development, and is essential for the maintenance of homeostasis. The biochemical event that is believed to irreversibly commit a cell to apoptosis is the activation of caspases (cysteine proteases cleaving after aspartic residues). Cells undergoing apoptosis display characteristic morphological and biochemical changes, including membrane blebbing, cell rounding, chromatin condensation, DNA cleavage, expression of apoptotic markers at the cell surface and inhibition of anti-apoptotic signaling pathways. All these events can be blocked by specific caspase inhibitors. It is thus the cleavage of the caspase substrate that is responsible for most, if not all, of the characteristic changes observed during apoptosis.

The execution phase of apoptosis is triggered when caspase substrates in a cell are cleaved. Dozens of caspase substrates have been identified and the list is growing steadily (Earnshaw W. C. et al., "Mammalian caspases: structure, activation, substrates, and functions during apoptosis" Annu. Rev. Biochem. 68, 383, 1999). Once cleaved, caspase substrates mediate the biochemical and morphological events observed during apoptosis such as amplification of the activation of caspases, DNA fragmentation, nuclear breakdown, etc.

Furthermore, Mitogen-activated protein kinase (MAPK) pathways have been shown to regulate apoptosis in a positive or negative manner (Jarpe M. B. et al., "Anti-apoptotic versus pro-apoptotic signal transduction: checkpoints and stop signs along the road to death" Oncogene, 17, 1475, 1998; Widmann C. et al, "Mitogen-activated protein kinase: conservation of a three-kinase module from yeast to human" Physiol. Rev. 79, 143, 1999). This could explain why the apoptotic caspases target some of the signaling proteins that regulate MAPK and/or are components of MAPK pathways (Widmann C. et al., "Caspase-dependent cleavage of signaling proteins during apoptosis. A turn-off mechanism for anti-apoptotic signals" J. Biol. Chem., 273, 7141, 1998). These proteins include MEKK1, PAK2, Mst1 and RasGAP.

Recently, Yang and Widmann, (Yang J.-Y. and Widmann C., "Antiapoptotic signaling generated by caspase-induced cleavage of RasGAP" Mol. Cell. Biol., 21, 5346, 2001; "A subset of caspase substrates functions as the Jekyll and Hyde of apoptosis" Eur. Cytokine Netw., 13, 387, 2002a; "The RasGAP N-terminal fragment generated by caspase cleavage protects cells in a Ras/PI3K/Akt-dependent manner that does not rely on NFkappa B" J. Biol. Chem., 277, 14641, 2002b), have demonstrated that RasGAP, a regulator of Ras and Rho GTP-binding proteins, is an unconventional caspase substrate because it can induce both anti- and pro-apoptotic signals, depending on the extent of its cleavage by caspases. They have shown that at low levels of caspase activity, RasGAP is cleaved at position 455, generating an N-terminal sequence (sequence N) and a C-terminal sequence (sequence C).

Sequence C, but not full-length RasGAP, induced a strong apoptotic response in HeLa cells as assessed by its ability to induce the appearance of pycnotic nuclei, activation of caspase 3, and cleavage of PARP.

In the same study, the authors have also shown that sequence N, rather than promoting cell death, appears to be a general blocker of apoptosis downstream of caspase activation. At higher levels of caspase activity, the ability of sequence N to counteract apoptosis is suppressed when it is cleaved at position 157. This latter cleavage event generates two sequences, N1 and N2, that in contrast to sequence N, have been shown to seitizises cells which can develop high caspase activities toward apoptosis induced by cisplatin, a drug used in chemotherapy to treat cancers.

However, it has been shown in Leblanc et al (Leblanc V. et al., "Ras-GTPase activating protein inhibition specifically induces apoptosis of tumour cells" Oncogene, 18, 4884, 1999) that injection of a monoclonal antibody directed against the SH3 domain of the N2 sequence of RasGAP in order to inhibit this protein specifically induces apoptosis in cancer cells. It is also know from patent application WO99/65947 (Parker et al.) that monoclonal antibodies directed against a RasGAP SH3-domain-binding protein, G3BP, induce apoptosis in cancer cells in which G3BP is specifically overexpressed.

These results seem to indicate that the RasGAP pathway regulating growth, through the RasGAP SH3 domain, is essential for some cancer cells to survive. These findings seem to be in contrast with the results obtained by Yang and Widmann thus leading to the conclusion that the RasGAP SH3 domain has a quite ambivalent function in the induction and regulation of apoptosis in cells.

Chemotherapy, alone or in combination with other treatments (e.g. radiotherapy), are currently one of the most common and efficient therapeutical tool to treat cancers. The efficacy of the drugs used in chemotherapy to treat cancers relies on their ability to kill cancer cells. There is, however, a limitation in the use of these drugs that comes from the fact that they can also adversely affect normal cells, non cancer cells, since they not only induce a strong stimulation of caspases in cancer cells but also in normal cells, non cancer cells, especially those cells that divide quickly.

Therefore, the challenge for the clinicians is to choose the doses of drugs that are high enough to eliminate the tumors but not so high as to induce severe side effects in the patients such as hair loss, nausea and vomiting, cardiac toxicity and secondary cancers.

Improving the selectivity of drugs towards cancer cells would obviously increase the efficacy of chemotherapeutic treatments thereby enabling lower doses of drugs. This will also result in reducing as far as possible the severe above-listed side effects.

Therefore, the object of the present invention is to provide an improved approach, in combination with a drug, for the treatment or prevention of cancers, which does not have the above-mentioned drawbacks.

SUMMARY OF THE INVENTION

This object has been achieved by providing a peptide consisting essentially of the N2 sequence of the RasGAP protein, a fragment thereof, or a variant thereof, which enhances the ability of a drug to kill selectively cancer cells.

Furthermore, the invention provides a purified and isolated nucleic acid sequence encoding the peptide, an expression vector comprising at least one copy of purified and isolated nucleic acid sequence and a eukaryotic or prokaryotic host cell containing the peptide, the isolated and purified nucleic acid sequence and/or the expression vector.

The invention further provides a pharmaceutical composition comprising as an active substance a pharmaceutically effective amount of at least one peptide according to the invention.

HeLa cells ($2\times10^6$) were plated in 10-cm-diameter Petri dishes, transfected with 1 µg of GFP-expressing plasmid (to label the transfected cells) together with 2 µg of an empty pcDNA3 plasmid or 2 µg of a pcDNA3 vector encoding fragment N2. One day following the transfection, the cells were incubated for 24 hours with the indicated concentrations of cisplatin, adriamycin or mitoxantrone. The number of GFP-positive cells displaying pycnotic nucleus was then scored.

The results correspond to the mean±standard deviation of three independent determinations. Asterisks denote significant differences between control cells and cells treated with cisplatin (*, $p<0.05$; , $p<0.01$; *, $p<0.001$).

Figure 2:
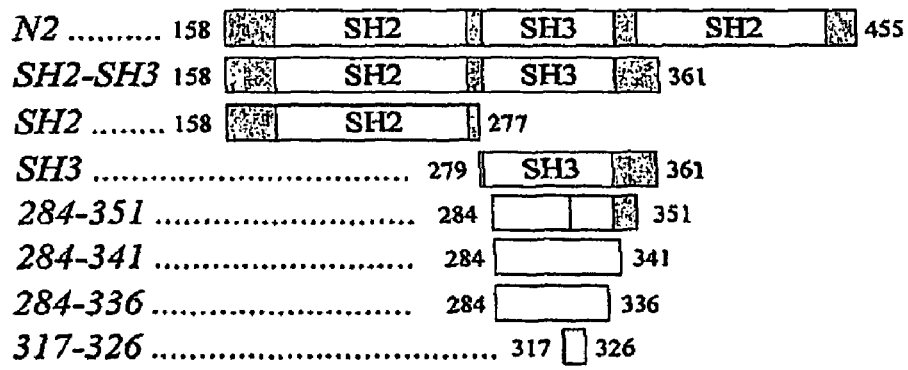
Figure 2:
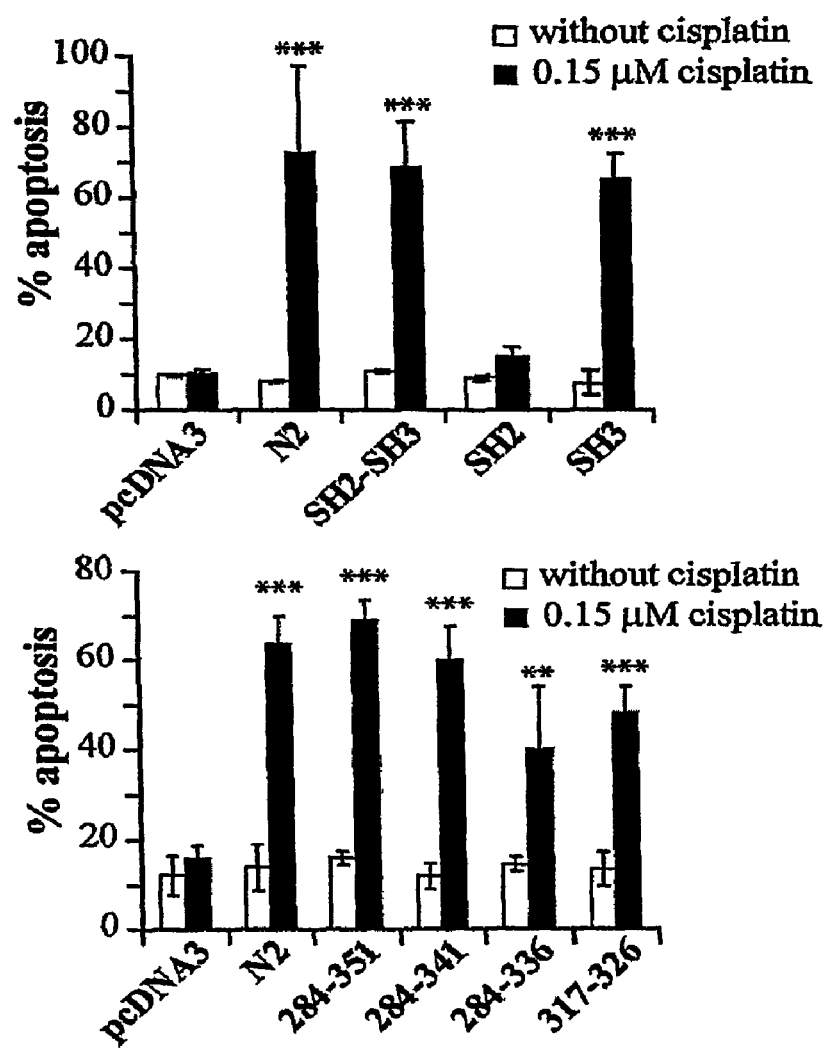

FIG. 2A is a schematic representation of the different constructs used in this study.

SH represents the Src homology domain.

FIG. 2B shows the percentage of apoptosis induction by cisplatin in HeLa cells transfected with plasmids encoding the constructs described in FIG. 2A.

Figure 1:
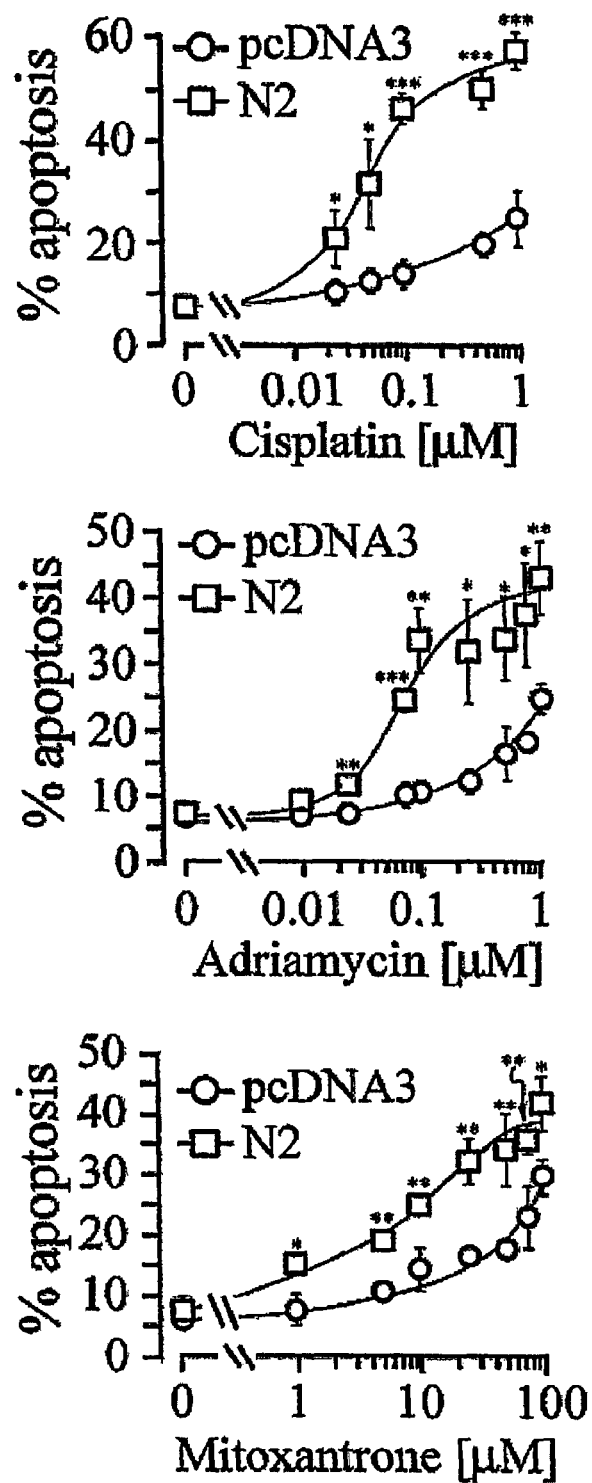
FIG. 1 shows the percentage of apoptosis induction by various drugs in HeLa cells transfected either with Fragment N2 or an empty pcDNA plasmid.

HeLa cells were transfected as described in FIG. 1 with plasmids endoding the constructs described in FIG. 2A. HeLa cells were then treated or not with 0.15 µM cisplatin and the extent of apoptosis was determined 20 hours later. The results correspond to the mean±standard deviation of three independent determinations. Asterisks denote a significant difference between the cells treated with 0.15 µM cisplatin and the cells without treatment (, $p<0.01$; *, $p<0.001$).

Figure 3:
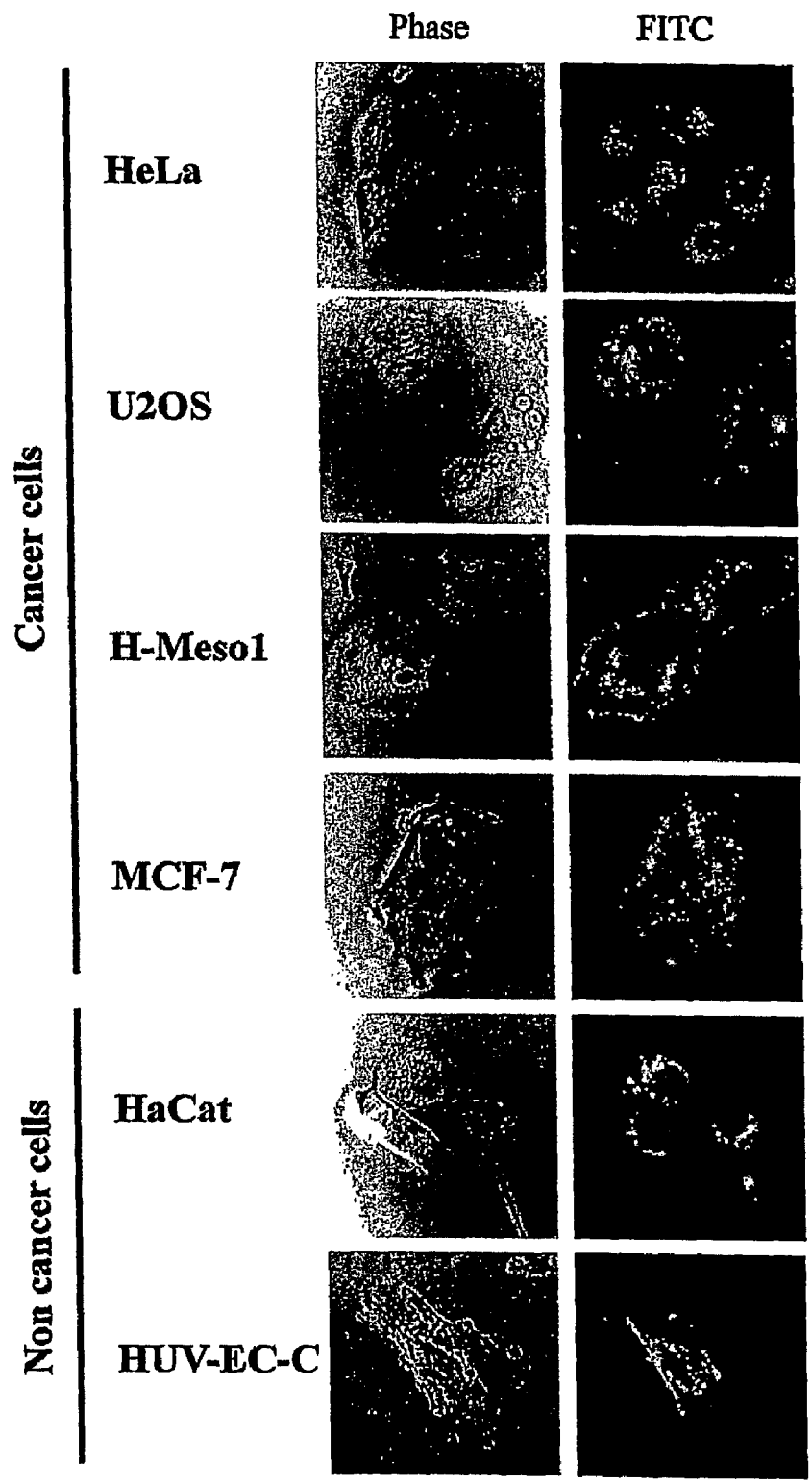

FIG. 3 shows phase contrast and epifluorescence images of ilve cells incubated with FITC-labelled TAT-RasGAP$_{317-326}$ peptide.

The following cell lines (HeLa, U2OS, H-Meso1, MCF-7, HaCat and HUV-EC-C) were incubated 3 hours at 37° C., 5% $CO_2$ in culture medium with 20 µM FITC-labelled TAT-RasGAP$_{317-326}$ peptide and then washed three times with culture medium.

Figure 4:
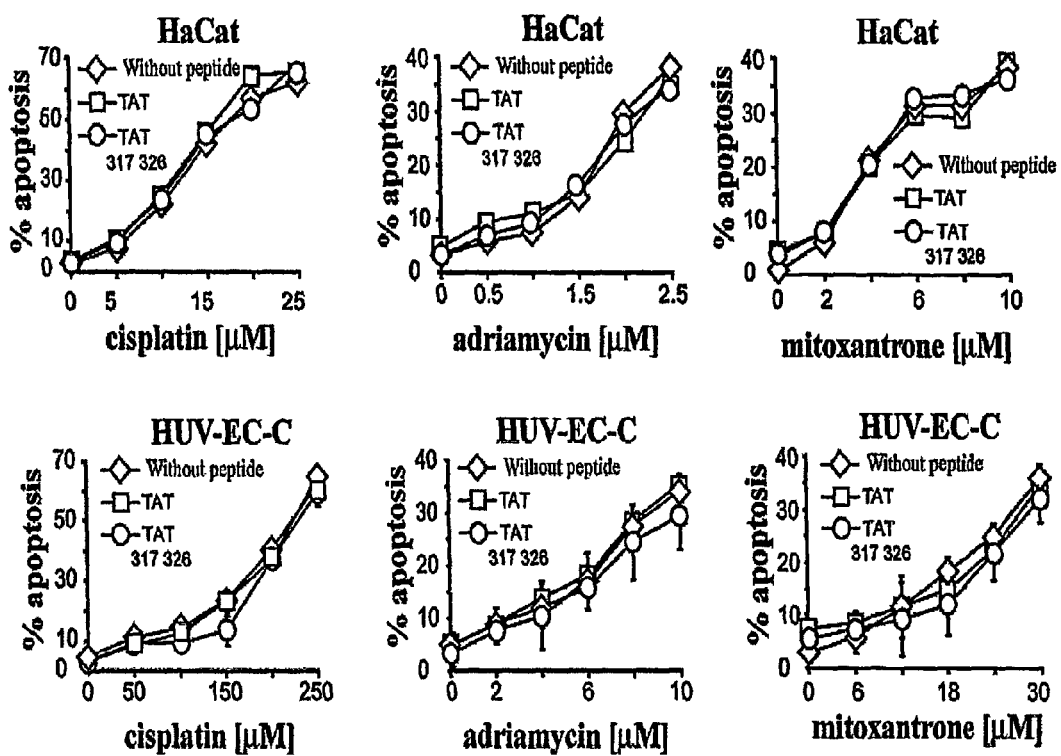
Figure 4:
Figure 4:
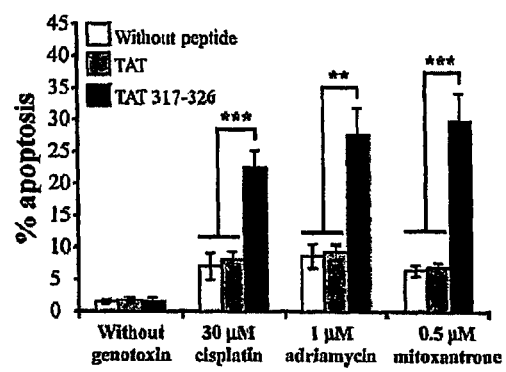
Figure 4:
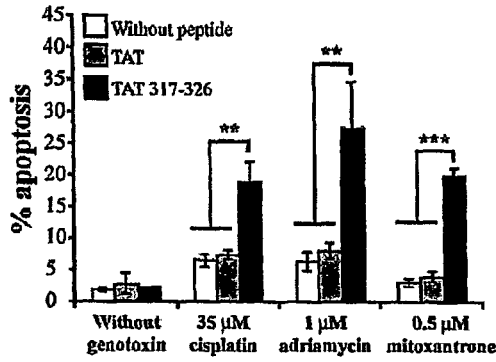
Figure 4:
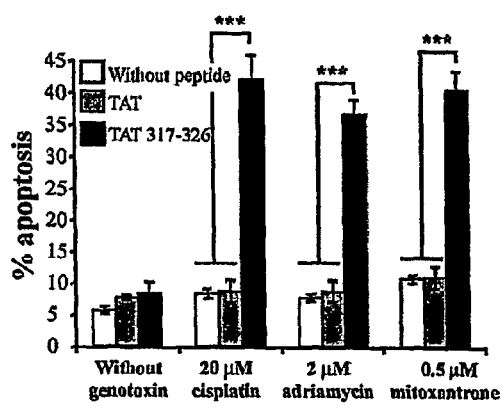

FIG. 4A shows the percentage of apoptosis induction by various drugs in two non-cancer cells treated or not with TAT-RASGAP$_{317-326}$.

Two non-cancer cell lines (HaCat and HUV-EC-C) were incubated with increasing concentrations of cisplatin, adriamycin and mitoxantrone in the absence or in the presence of 20 µM TAT-RaasGA-P$_{317-326}$. The extent of apoptosis was scored 20 hours later.

FIG. 4B shows the percentage of apoptosis induction by various drugs in four cancer cell lines treated or not with TAT-RASGAP$_{317-326}$.

Four cancer cell lines (HeLa, U2OS, MCF-7, and H-Meso1) were plated in 6-wells plates and treated with the indicated concentrations of cisplatin, adriamycin and mitoxantrone in the absence or in the presence of either 20 µM MV-TAT$_{48-57}$ Or TAT-RaSGAP$_{317-326}$ peptides for 20 hours. The number of cells displaying pycnotic nucleus was then scored. The results correspond to the mean±standard deviation of three independent determinations. Asterisks denote significant differences between the genotoxin-treated cells incubated with TAT-RaSGAP$_{317-326}$ and those left untreated or incubated with the HIV-TAT$_{48-57}$ peptide (, $p<0.01$; *, $p<0.001$).

Figure 5:
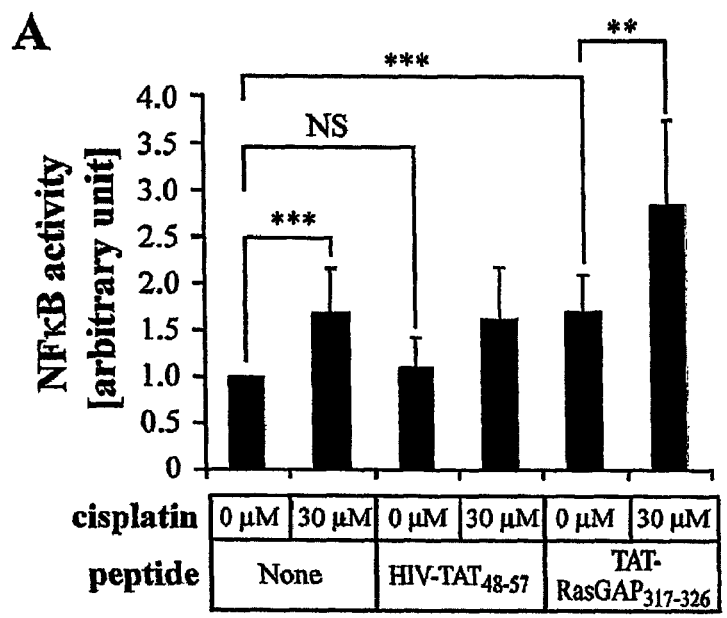
Figure 5:
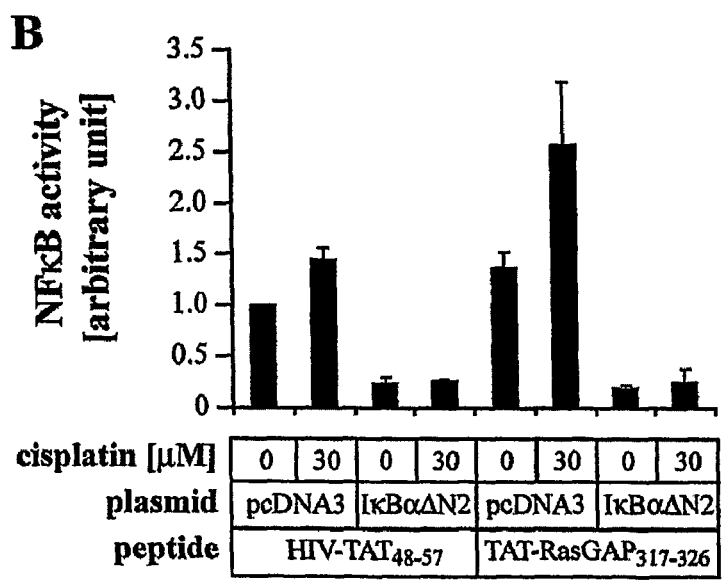
Figure 5:
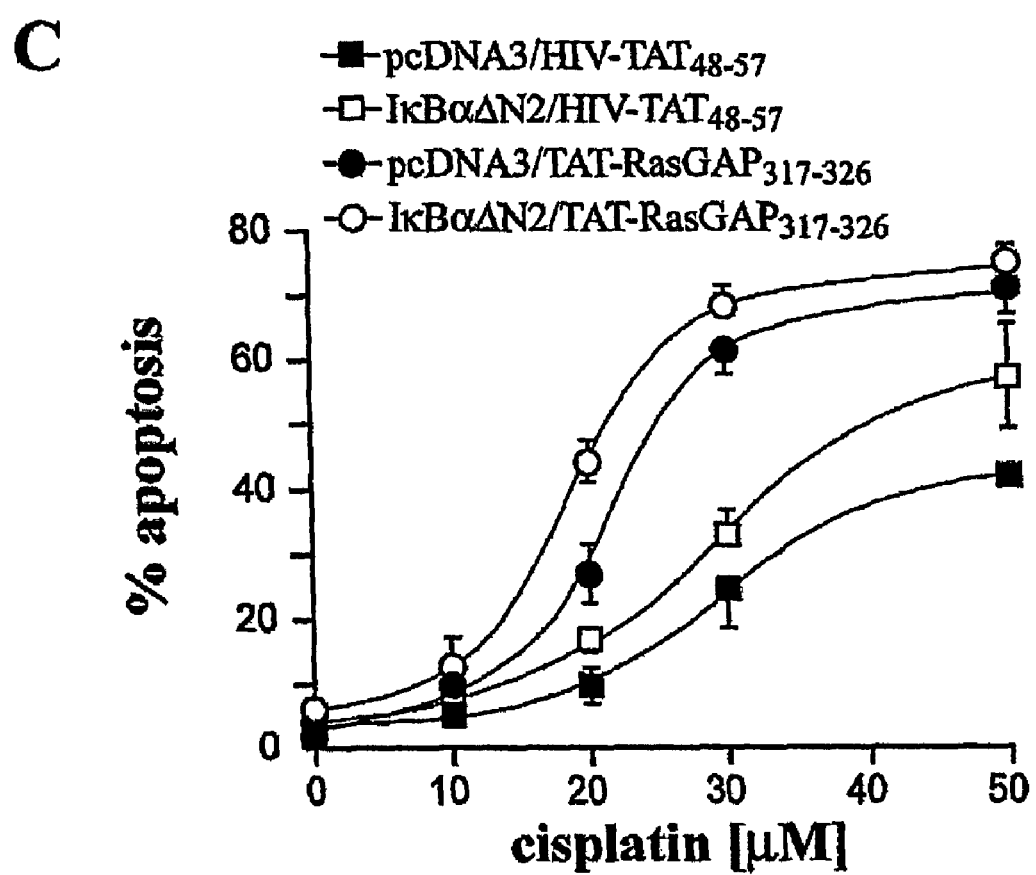

FIG. 5A shows the NFκB activity in U2OS cells treated with cisplatin and in the presence of HIV-TAT$_{48-57}$ or TAT-RaSGAP$_{317-326}$ peptides U2OS Cells ($1\times10^5$) were plated in 6 well plates and transfected with 1 µg of a firefly luciferase reporter plasmid for NFκB activity and 0.1 µg of a plasmid encoding the Renilla luciferase. The cells were treated one day later with the indicated concentrations of cisplatin in the absence or in the presence of 20 µM HV-TAT$_{48-57}$ or TAT-RaSGAP$_{317-326}$ peptides during 20 hours. The data represent the firefly luciferase activity normalized to the Renilla luciferase activity and expressed as fold increase of the basal NFκB activity obtained in control untreated cells. The results correspond to the mean±standard deviation of three independent determinations. Asterisks denote significant differences between the indicated conditions (, $p<0.01$; *, $p<0.001$).

FIG. 5B shows the NFκB activity in U2OS cells treated with cisplatin and in the presence of HIV-TAT$_{48-57}$ peptide and IκBαΔN2 or TAT-RasGAP$_{317-326}$ peptide and IκBαΔN2.

U2OS cells were transfected with 1 µg of a firefly luciferase reporter plasmid for NFκB activity, 0.1 µg of a plasmid encoding the Renilla luciferase, 0.5 µg of a GFP-expressing plasmid (to label the transfected cells), 1 µg of a plasmid encoding IκBαΔN2 that inhibit the NFκB pathway or with 1 µg an empty pcDNA3 vector. The cells were incubated one day later with increasing concentrations of cisplatin in the presence of 20 µM HIV-TAT$_{48-57}$ or 20 µM TAT-Ras GAP$_{317-326}$ for an additional 20 hour period. The cells were then lysed and the NFκB activity assessed as described in panel A, except that the results were expressed as fold increase of the NFκB activity detected in cells incubated with the control HV-TAT$_{48-57}$ peptide.

FIG. 5C shows the percentage of apoptosis of transfected cells of FIGS. 5A and B.

Alternatively, the number of GFP-positive cells displaying pycnotic nucleus was determined. The results correspond to the mean±standard deviation of three independent determinations.

Figure 6:
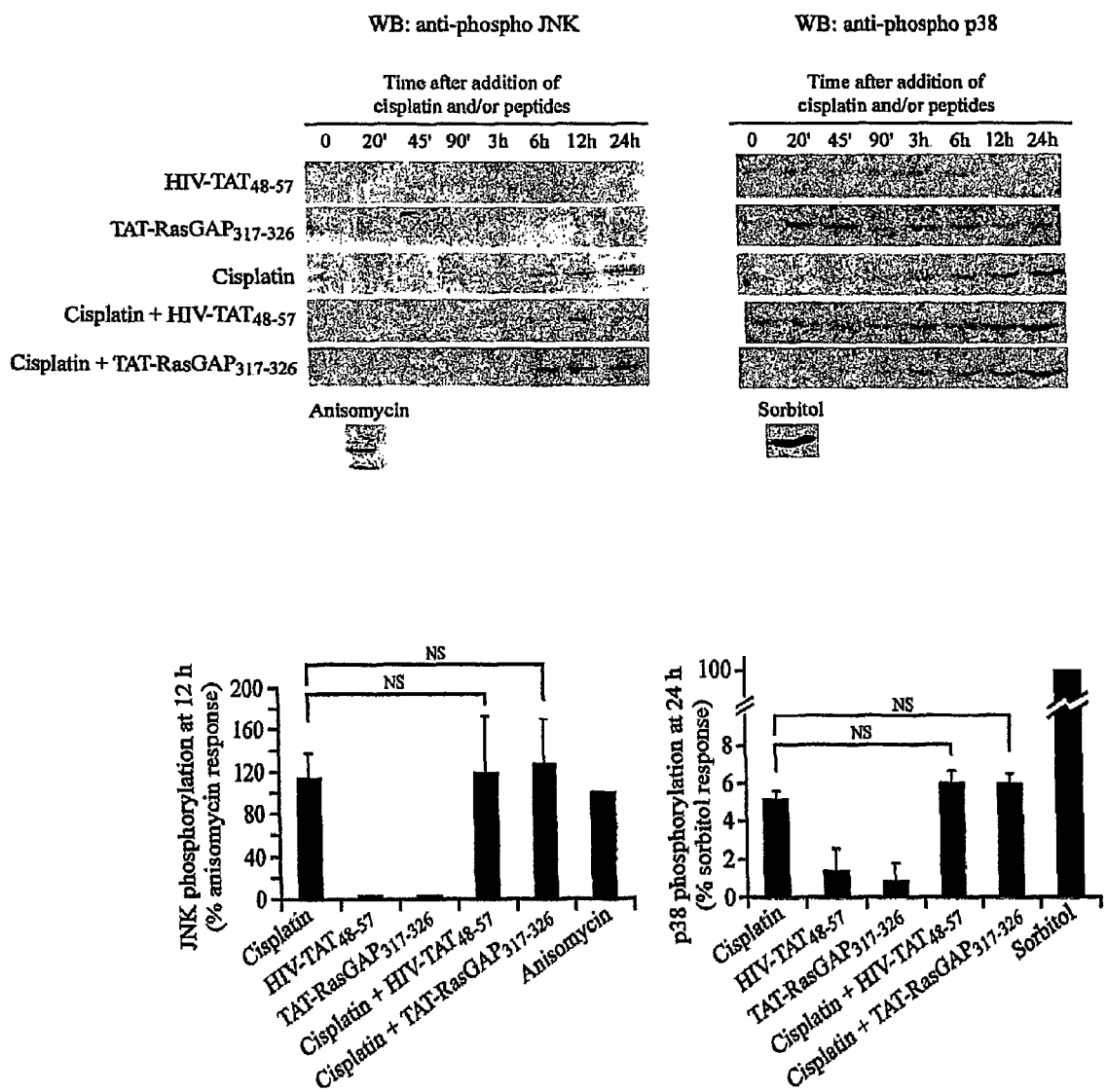

FIG. 6 represents western blots and percentage of JNK phosphorylations of U2OS cells transfected with either HIV-TAT$_{48-57}$ or TAT-RasGAP$_{317-326}$ peptides and treated with cisplatin.

U2OS cells ($2\times10^5$) were plated in 6 well plates and treated for the indicated periods of time with the indicated combinations of the HW-TAT$_{48-57}$ or TAT-RasGAP$_{317-326}$ peptides (at a 20 µM concentration) and cisplatin (at a 30 µM concentration). Positive controls for JNK and p38 activation were obtained following stimulation of the cells with 1 µg/ml anisomycine during 3 hours and with 0.5 M sorbitol for 30 min, respectively. The quantitations depicted under the Western blots were performed on the 12-hour bands and normalized against the positive controls. The results correspond to the mean±standard deviation of three independent experiments.

DETAILED DESCRIPTION OF THE INVENTION

As used herein, the terms "peptide", "protein", "polypeptide", "polypeptidic" and "peptidic" are used interchangeably to designate a series of amino acid residues connected to the other by peptide bonds between the alpha-amino and carboxy groups of adjacent residues.

RasGAP, a regulator of Ras and Rho GTP-binding proteins, is an unconventional caspase substrate because it can induce both anti- and pro-apoptotic signals, depending on the extent of its cleavage by caspases. At low levels of caspases, RasGAP is cleaved at position 455, generating an N-terminal fragment (fragment N, of about 56 kD) and a C-terminal fragment (fragment C, of about 64 kD). Fragment N appears to be a general blocker of apoptosis downstream of caspase activation (Yang J.-Y. and Widmann C., Mol. Cell. Biol., 21, 5346, 2001 and J. Biol. Chem., 277, 14641, 2002b). At high levels of caspase activity, fragment N is further cleaved at position 157 thus generating two fragments, N1 (amino acids 1 to 157) and N2 (amino acids 158 to 455).

By "cancer cell" is meant a cell arising in an animal in vivo which is capable of undesired and unregulated cell growth or abnormal persistence or abnormal invasion of tissues. In vitro this term also refers to a cell line that is a permanently immortalized established cell culture that will proliferate indefinitely and in an unregulated manner given appropriate fresh medium and space.

The term "drug" refers to drugs which are able to kill mammalian cells, preferably human cells. There are several classes of drugs of different origin and with different modes of action.

Drugs of the present invention concern agents which are derived from, or which beneficially modulate host biological processes. Interferons, tumor growth factors, tumor necrosis factors, growth factors such as GM-CSF and G-CSF and interleukins such as interleukin-2, interleukin-6, interleukin-7 and interleukin-12 are examples of such biological drugs currently used in cancer therapeutics.

A drug of the present invention can concern as well agents which damage DNA and/or prevent cells from multiplying, such as genotoxins. Genotoxins can be selected from the group comprising alkylating agents, antimetabolites, DNA cutters, DNA binders, topoisomerase poisons and spindle poisons.

Examples of alkylating agents are lomustine, carmustine, streptozocin, mechlorethamine, melphalan, uracil nitrogen mustard, chlorambucil, cyclosphamide, iphosphamide, cisplatin, carboplatin, mitomycin, thiotepa, dacarbazin, procarbazine, hexamethyl melamine, triethylene melamine, busulfan, pipobroman, mitotane and other platine derivatives.

An example of DNA cutters is bleomycin.

Toposiomerases poisons can be selected from the group comprising topotecan, irinotecan, camptothecin sodium salt, daorubicin, doxorubicin, idarubicin, mitoxantrone tenipo-side, adriamycin and etoposide.

Examples of DNA binders are dactinomycin and mithramycin whereas spindle poisons can be selected among the group comprising vinblastin, vincristin, navelbin, paclitaxel and docetaxel.

As drug as well antimetabolites can be used which can be selected among the following coumpounds: methotrexate, trimetrexate, pentostatin, cytarabin, ara-CMP, fludarabine phosphate, hydroxyurea, fluorouracyl, floxuridine, chlorodeoxyadenosine, gemcitabine, thioguanine and 6-mercaptopurine.

Preferably a genotoxin, more preferably cisplatin, mitoxantrone and adriamycin are used as drug in the present invention.

These drugs can be used alone or in combination with one another. In case more than one drug is used the determination of a useful combination of drugs is well within the capabilities of those skilled in the art, and will depend e. g. on the cancer cells to kill.

The term "enhancing" as used herein refers to the capacity of a peptide to increase the effect of a drug to kill cells. This capacity can be measured in vitro by, for example, measuring the percentage of apoptosis of cells containing a peptide and treated with at least one drug by scoring the number of cells displaying pycnotic nuclei (a marker of apoptotic cells). Typically, the results are compared to those from drug-treated cells that do not contain said peptide. A peptide that leads to a two fold or more increase of apoptosis in cells at a given concentration or that decreases by at least two-fold the dose of a drug to induce a given apoptotic response, will be considered as enhancing the ability of a drug to kill cells.

As used herein, by the term "selectively" is meant that the peptide of the invention enhances the ability of a drug to kill cells at a given concentration, specifically in cancer cells but surprisingly not in non cancer cells.

Concentration ranges of a drug in vitro in which the peptide enhances the ability of a drug to kill cells selectively in cancer cells depend, usually, on the drug used. For example, in case a genotoxin is used, usually the concentration of the drug in vitro is between 0.1 to 100 µM, preferably between 0.15 to 30 µM.

The N2 sequence of the RasGAP protein is preferably derived from human and refers to a 36 kD protein consisting of 297 amino acids which encompasses two SH2 and one SH3 domain as shown in FIG. 2A.

In general, Src homology 2 (SH2) domains are involved in recognition of phosphorylated tyrosine whereas Src homology 3 (SH3) domains are often indicative of a protein involved in signal transduction related to cytoskeletal organisation.

"Fragment" refers to a sequence containing less amino acids in length than the N2 sequence of the RasGAP protein. This sequence can be used as long as it exhibits the same properties as the native sequence from which it derives. Preferably this sequence contains less than 90%, preferably less than 60%, in particular less than 30% amino acids in length than the respective N2 sequence of the RasGAP protein.

The present invention also includes a variant of the N2 sequence of the RasGAP protein. The term "variant" refers to a peptide having an amino acid sequence that differ to some extent from a native sequence peptide, that is an amino acid sequence that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln IV. Large, aromatic residues: Phe, Tyr, Trp
V. Large, aliphatic, nonpolar residues: Met, Leu, Ile, Val, Cys.

The N2 sequence, as well as a fragment and a variant thereof can be prepared by a variety of methods and techniques known in the art such as for example chemical synthesis or recombinant techniques as described in Maniatis et al. 1982, Molecular Cloning, A laboratory Manual, Cold Spring Harbor Laboratory.

Preferably, the fragment of the N2 sequence of the Ras-GAP protein comprises the amino acid sequence of the SH3 domain of the N2 sequence, a part thereof, or a variant thereof.

Applicants, surprisingly, have characterized a shorter sequence of the N2 sequence of the RasGAP protein that still enhances the ability of a drug to kill selectively cancer cells and that has also the advantage to be more easily synthesized. In order to assess whether such a part thereof could be isolated, applicants have generated a series of truncated versions of fragment N, as shown in FIG. 2A and determined their ability to potentiate drug induced apoptosis in a cancer cell line (FIG. 2B). These parts of the N2 sequence have been cloned into a vector and transfected into a cancer cell line (HeLa).

Applicants have shown that HeLa cells transfected with an empty construct or with a construct encoding the SH2 domain of N2 only do not enhance cisplatin-induced death. In contrast, cells expressing the constructs containing the SH3 domain had an increased enhancement of cisplatin-induced apoptosis as shown in FIG. 2B Applicants have then generated progressive truncations in the SH3 domain in an attempt to identify a minimal enhancing sequence. All these constructs or parts of the N2 sequence (FIG. 2A), including the shortest one (317-326) that codes for a 10 amino acid long peptide, potentiated the ability of cisplatin to kill HeLa cells (FIG. 2B). These results show that the cell-death enhancing property of fragment N2 does not require a complete SH3 domain but is mediated by a part of the SH3 domain such as a short peptidic sequence.

The part of the SH3 domain or the variant thereof contains preferably less than or equal to 70, more preferably less than or equal to 30, most preferably less than or equal to 10 amino acids of the amino acid sequence of the SH3 domain.

In particular encompassed by the present invention is a part of the SH3 domain which consists in the amino acid sequences encoded by the DNA sequences of Table 1:

TABLE 1

| Sequences | Name | DNA sequences | Amino Acid sequences |
|---|---|---|---|
| SEQ ID N° 1 | RasGAP$_{284-351}$ | gaagatagaaggcgtgtacgagctattctacctta cacaaaagtaccagacactgatgaaataagtttct taaaaggagatatgttcattgttcataatgaatta gaagatggatggatgtgggttacaaatttaagaac agatgaacaaggccttattgttgaagacctagtag aagaggtgggccgggaagaagatccacatgaagga aaaatatggttccatgggaagatttccaaacagga agct | EDRRRVRAILPYTKV PDTDEISFLKGDMFI VHNELEDGWMWVTNL RTDEQGLIVEDLVEE VGREEDPHEGKIWFH GKISKQEA |
| SEQ ID N° 2 | RasGAP$_{284-341}$ | gtacgagctattctaccttacacaaaagtaccaga cactgatgaaataagtttcttaaaaggagatatgt tcattgttcataatgaattagaagatggatggatg tgggttacaaatttaagaacagatgaacaaggcct tattgttgaagacctagtagaagaggtgggccggg aagaagatccacatgaaggaaaaatatgg | RVRAILPYTKVPDTD EISFLKGDMFIVHNE LEDGWMWVTNLRTDE QGLIVEDLVEEVGRE EDPHEGKIW |
| SEQ ID N° 3 | RasGAP$_{284-336}$ | gtacgagctattctaccttacacaaaagtaccaga cactgatgaaataagtttcttaaaaggagatatgt tcattgttcataatgaattagaagatggatggatg tgggttacaaatttaagaacagatgaacaaggcct tattgttgaagacctagtagaagaggtgggccggg | RVRAILPYTKVPDTD EISFLKGDMFIVHNE LEDGWMWVTNLRTDE QGLIVEDLVEEVGR |
| SEQ ID N° 4 | RasGAP$_{317-326}$ | tggatgtgggttacaaatttaagaacagat | WMWVTNLRTD |

In case the part of the SH3 domain of the N2 sequence is SEQ ID NO: 4 (RasGAP$_{317-326}$) then the resulting amino acid sequence encoded by said SEQ ID NO: 4 in human is WMWVTNLRTD (SEQ ID NO: 8). A comparison between the different species revealed that there are different amino acids, which are conserved among the species as shown in table 2.

TABLE 2

| Species | Amino acid sequences of RasGAP$_{317-326}$ |
|---|---|
| Human | WMWVTNLRTD |
| Bos taurus | WMWVTNLRTD |
| Mouse | WMWVTNLRTD |
| Rattus norvegicus | WMWVTNLRTD |
| Anopheles | WLWVTAHRTG |
| Drosophila | WLWVTAHRTG |
| Alignment | WxWVTxxRTx |

Conserved amino acids among the species are represented as bold underlined type residues whereas the X correspond to amino acid residues that can be changed by conservative, or non-conservative amino acid substitutions, without impairing the inventive properties of these 10 amino acid parts of the SH3 domain of N2.

These peptidic variants of this 10 amino acid part of the human SH3 domain of N2, and in particular the alignment sequence WXWVTXXRTX (SEQ ID NO: 14), are also encompassed by the present invention and they refer to peptides having an amino acid sequence that differ to some extent from the native sequence peptide, that is the amino acid sequence that vary from the native sequence WMWVTNL-RTD (SEQ ID NO: 8) by conservative or non-conservative amino acid substitutions, whereby one or more amino acid residues are substituted by another with same characteristics and conformational roles.

Usually, the peptide consisting essentially of the N2 sequence of the RasGAP protein, a fragment thereof, or a variant thereof as disclosed in the present invention is conjugated to an agent which increases the accumulation of the peptide in a cell.

Such an agent can be a compound which induces receptor mediated endocytose such as for example the membrane transferrin receptor mediated endocytosis of transferrin conjugated to therapeutic drugs (Qian Z. M. et al., "Targeted drug delivery via the transferrin receptor-mediated endocytosis pathway" Pharmacological Reviews, 54, 561, 2002) or a cell membrane permeable carrier which can, be selected e. g. among the group of fatty acids such as decanoic acid, myristic acid and stearic acid, which have already been used for intracellular delivery of peptide inhibitors of protein kinase C (Ioannides C. G. et al., "Inhibition of IL-2 receptor induction and IL-2 production in the human leukemic cell line Jurkat by a novel peptide inhibitor of protein kinase C" Cell Immunol., 131, 242, 1990) and protein-tyrosine phosphatase (Kole H. K. et al., "A peptide-based protein-tyrosine phosphatase inhibitor specifically enhances insulin receptor function in intact cells" J. Biol. Chem. 271, 14302, 1996) or among peptides. Preferably, cell membrane permeable carriers are used, more preferably a cell membrane permeable carrier peptide is used.

In case the cell membrane permeable carrier is a peptide then it will preferably be an arginine rich peptide. It has been recently shown in Futaki et al. (Futaki S. et al., "Arginine-rich peptides. An abundant source of membrane-permeable peptides having potential as carriers for intracellular protein delivery" J. Biol. Chem., 276, 5836, 2001), that the number of arginine residues in a cell membrane permeable carrier peptide has a significant influence on the method of internalization and that there seems to be an optimal number of arginine residues for the internalization, preferably they contain more than 6 arginines.

The peptide of the invention is usually conjugated to the cell membrane permeable carrier by a spacer. In this case the cell membrane permeable carrier is preferably a peptide.

Usually arginine rich peptides are selected from the group comprising the HIV-TAT$_{48-57}$ peptide, the FHV-coat$_{35-49}$ peptide, the HTLV-II Rex$_{4-16}$ peptide and the BMV gag$_{7-25}$ peptide. Preferably, the arginine rich peptide is HIV-TAT$_{48-57}$ peptide.

In case the HIV-TAT$_{48-57}$ peptide is conjugated to a RasGAP sequence, such as for example RasGAP$_{317-326}$, then two glycine residues are inserted between the TAT and RasGAP sequences as spacer to allow flexibility.

Since an inherent problem with native peptides (in L-form) is degradation by natural proteases, the peptide of the invention may be prepared to include D-forms and/or "retro-inverso isomers" of the peptide.

In this case, retro-inverso isomers of short fragments and variants of the peptide of the invention are prepared.

Protecting the peptide from natural proteolysis should therefore increase the effectiveness of the specific heterobivalent or heteromultivalent compound. A higher biological activity is predicted for the retro-inverso containing peptide when compared to the non-retro-inverso containing analog owing to protection from degradation by native proteinases. Furthermore they have been shown to exhibit an increased stability and lower immunogenicity (Sela M. and Zisman E., "Different roles of D-amino acids in immune phenomena" FASEB J. 11, 449, 1997).

Retro-inverso peptides are prepared for peptides of known sequence as described for example in Sela and Zisman, (1997).

By "retro-inverso isomer" is meant an isomer of a linear peptide in which the direction of the sequence is reversed and the chirality of each amino acid residue is inverted; thus, there can be no end-group complementarity.

Also encompassed by the present invention are modifications of the peptide (which do not normally alter primary sequence), including in vivo or in vitro chemical derivitization of peptides, e. g., acetylation or carboxylation. Also included are modifications of glycosylation, e. g., those made by modifying the glycosylation patterns of a peptide during its synthesis and processing or in further processing steps, e. g., by exposing the peptide to enzymes which affect glycosylation e. g., mammalian glycosylating or deglycosylating enzymes. Also included are sequences which have phosphorylated amino acid residues, e. g., phosphotyrosine, phosphoserine, or phosphothreonine.

The invention also includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as an active substance. Such mimetics, and methods of incorporating them into peptides, are well known in the art.

Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

When recombinant techniques are employed to prepare a peptide consisting essentially of the N2 sequence of the RasGAP protein, a fragment thereof, or a variant thereof, in accordance with the present invention, nucleic acid sequences encoding the polypeptides are preferably used. With regard to the method to practise recombinant techniques, see for example, Maniatis et al. 1982, Molecular Cloning, A laboratory Manual, Cold Spring Harbor Laboratory and commercially available methods.

Therefore the present invention also relates to a purified and isolated nucleic acid sequence encoding a peptide consisting essentially of the N2 sequence of the RasGAP protein, a fragment thereof, or a variant thereof as described above.

"A purified and isolated nucleic acid or nucleic acid sequence" refers to the state in which the nucleic acid sequence encoding the peptide of the invention, or nucleic acid encoding such peptide consisting essentially of the N2 sequence of the RasGAP protein, a fragment thereof, or a variant thereof will be, in accordance with the present invention.

A purified and isolated nucleic acid or nucleic acid sequence encompassed by the present invention might be DNA, RNA, or DNA/RNA hybrid.

DNA which can be used herein is any polydeoxynucleotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid.

DNA sequences that encode a peptide consisting essentially of the N2 sequence of the RasGAP protein, a fragment thereof, or a variant thereof, can be synthesized by standard chemical techniques, for example, the phosphotriester method or via automated synthesis methods and PCR methods.

The purified and isolated DNA sequence encoding a peptide consisting essentially of the N2 sequence of the RasGAP protein, a fragment thereof, or a variant thereof, according to the invention may also be produced by enzymatic techniques. Thus, restriction enzymes, which cleave nucleic acid molecules at predefined recognition sequences can be used to isolate nucleic acid sequences from larger nucleic acid molecules containing the nucleic acid sequence, such as DNA (or RNA) that codes for a peptide consisting essentially of the N2 sequence of the RasGAP protein, a fragment thereof, or a variant thereof.

Encompassed by the present invention is also a nucleic acid in the form of a polyribonucleotide (RNA), including, e.g., single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, MnRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

Preferably used as nucleic acid is a purified and isolated DNA sequence selected from the group comprising SEQ ID No 1, SEQ ID No 2, SEQ ID No 3, or SEQ ID No 4.

The present invention also includes variants of the aforementioned sequences, that is nucleotide sequences that vary from the reference sequence by conservative nucleotide substitutions, whereby one or more nucleotides are substituted by another with same characteristics.

The invention also encompasses allelic variants of the disclosed purified and isolated nucleic sequence; that is, naturally-occurring alternative forms of the isolated and purified nucleic acid that also encode peptides that are identical, homologous or related to that encoded by the purified and isolated nucleic sequences. Alternatively, non-naturally occurring variants may be produced by mutagenesis techniques or by direct synthesis.

The aforementioned purified and isolated nucleic acid sequence encoding a peptide consisting essentially of the N2 sequence of the RasGAP protein, a fragment thereof, or a variant thereof, may further comprise a nucleotide sequence encoding a cell membrane permeable carrier peptide.

Yet another concern of the present invention is to provide an expression vector comprising at least one copy of the isolated and purified nucleic acid sequence encoding a peptide consisting essentially of the N2 sequence of the RasGAP protein, a fragment thereof, or a variant thereof as described above. Preferably the isolated and purified nucleic acid sequence encoding a peptide of the invention is DNA.

As used herein, "vector", "plasmid" and "expression vector" are used interchangeably, as the plasmid is the most commonly used vector form.

The vector may further comprise a nucleotide sequence encoding a cell membrane permeable carrier peptide in accordance with the invention. The choice of an expression vector depends directly, as it is well known in the art, on the desired functional properties, e.g., peptide expression and the host cell to be transformed or transfected.

Additionally, the expression vector may further comprise a promoter operably linked to the purified and isolated DNA sequence. This means that the linked isolated and purified DNA sequence encoding the peptide of the present invention is under control of a suitable regulatory sequence which allows expression, i.e. transcription and translation of the inserted isolated and purified DNA sequence.

As used herein, the term "promoter" designates any additional regulatory sequences as known in the art e.g. a promoter and/or an enhancer, polyadenylation sites and splice junctions usually employed for the expression of the polypeptide or may include additionally one or more separate targeting sequences and may optionally encode a selectable marker. Promoters which can be used provided that such promoters are compatible with the host cell are e.g promoters obtained from the genomes of viruses such as polyoma virus, adenovirus (such as Adenovirus 2), papilloma virus (such as bovine papilloma virus), avian sarcoma virus, cytomegalovirus (such as murine or human cytomegalovirus immediate early promoter), a retrovirus, hepatitis-B virus, and Simian Virus 40 (such as SV 40 early and late promoters) or promoters obtained from heterologous mammalian promoters, such as the actin promoter or an immunoglobulin promoter or heat shock promoters.

Enhancers which can be used are e.g. enhancer sequences known from mammalian genes (globin, elastase, albumin, a-fetoprotein, and insulin) or enhancer from a eukaryotic cell virus. e.g. the SV40 enhancer, the cytomegalovirus early promoter enhancer, the polyoma, and adenovirus enhancers.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e. g., E. coli plasmids col E1, pCR1, pBR322, pcDNA3, pMB9 and their derivatives, plasmids such as RP4; phage DNAs, e. g., the numerous derivatives of phage X, e. g., NM989, and other phage DNA, e. g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Most preferably the expression vector is pcDNA3.

Another concern of the present invention is to provide a eukaryotic or prokaryotic host cell containing the peptide according to the invention, the isolated and purified nucleic acid sequence of the invention or and/or expression vector described herein.

Transformation or transfection of appropriate eukaryotic or prokaryotic host cells with an expression vector comprising a purified and isolated DNA sequence according to the invention is accomplished by well known methods that typically depend on the type of vector used. With regard to these methods, see for example, Maniatis et al. 1982, Molecular Cloning, A laboratory Manual, Cold Spring Harbor Laboratory and commercially available methods. The term "cell transfected" or "cell transformed" or "transfected/transformed cell" means the cell into which the extracellular DNA has been introduced and thus harbours the extracellular DNA. The DNA might be introduced into the cell so that the nucleic acid is replicable either as a chromosomal integrant or as an extra chromosomal element.

The peptide consisting essentially of the N2 sequence of the RasGAP protein, a fragment thereof, or a variant thereof, optionally conjugated to an agent which increases the accumulation of the peptide in a cell as described herein are preferably produced, recombinantly, in a cell expression system.

A wide variety of unicellular host cells are useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e. g., COS 1, COS 7, BSC1, BSC40, and BMT10), insect cells (e. g., Sf9), and human cells and plant cells in tissue culture. Preferably, the host cell is a bacterial cell, more preferably an *E. coli* cell.

The present invention is also directed to a pharmaceutical composition comprising as an active substance a pharmaceutically effective amount of at least one peptide as described, optionally in combination with pharmaceutically acceptable carriers, diluents and adjuvants.

"A pharmaceutically effective amount" refers to a chemical material or compound which, when administered to a human or animal organism induces a detectable pharmacologic and/or physiologic effect.

The respective pharmaceutically effect amount can depend on the specific patient to be treated, on the disease to be treated and on the method of administration. Further, the pharmaceutically effective amount depends on the specific peptide used, especially if the peptide additionally contains a drug as described or not. The treatment usually comprises a multiple administration of the pharmaceutical composition, usually in intervals of several hours, days or weeks. The pharmaceutically effective amount of a dosage unit of the polypeptide usually is in the range of 0.001 ng to 100 µg per kg of body weight of the patient to be treated.

Preferably, in addition to at least one peptide as described herein, the pharmaceutical composition may contain one or more pharmaceutically acceptable carriers, diluents and adjuvants.

Acceptable carriers, diluents and adjuvants which facilitates processing of the active compounds into preparation which can be used pharmaceutically are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes or via an implanted device, and may also be delivered by peristaltic means.

The pharmaceutical composition comprising a peptide, as described herein, as an active agent may also be incorporated or impregnated into a bioabsorbable matrix, with the matrix being administered in the form of a suspension of matrix, a gel or a solid support. In addition the matrix may be comprised of a biopolymer.

Sustained-release preparations may be prepared. Suitable examples of sustained-release preparations include semi permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile. This is readily accomplished for example by filtration through sterile filtration membranes.

It is understood that the suitable dosage of a peptide of the present invention will be dependent upon the age, sex, health, and weight of the recipient, kind of concurrent treatment, if any and the nature of the effect desired.

The appropriate dosage form will depend on the disease, the peptide, and the mode of administration; possibilities include tablets, capsules, lozenges, dental pastes, suppositories, inhalants, solutions, ointments and parenteral depots.

Since amino acid modifications of the amino acids of the peptide are also encompassed in the present invention, this may be useful for cross-linking the peptide of the invention to a water-insoluble matrix or the other macromolecular carriers, or to improve the solubility, adsorption, and permeability across the blood brain barrier. Such modifications are well known in the art and may alternatively eliminate or attenuate any possible undesirable side effect of the peptide and the like.

While a preferred pharmaceutical composition of the present invention comprises a peptide as an active agent, an alternative pharmaceutical composition may contain a purified and isolated nucleic acid sequence encoding the peptide, as described herein, as an active agent. This pharmaceutical composition may include either the sole purified and isolated DNA sequence, an expression vector comprising said purified and isolated DNA sequence or a host cell previously transfected or transformed with an expression vector described herein. In this latter example, host cell will preferably be isolated from the patient to be treated in order to avoid any antigenicity problem. These gene and cell therapy approaches are especially well suited for patients requiring repeated administration of the pharmaceutical composition, since the said purified and isolated DNA sequence, expression vector or host cell previously transfected or transformed with an expression vector can be incorporated into the patient's cell which will then produce the protein endogenously.

Usually, the pharmaceutical composition as described herein is used for the treatment or prevention of cancer.

Also encompassed by the present invention is the use of the pharmaceutical composition of the invention, for the preparation of a medicament for the treatment or prevention of cancer.

The term "cancer" refers to or describes the physiological condition in mammals that is typically characterized by unregulated cell growth.

Usually, the cancer to be treated or prevented will be selected from the group consisting of carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

Preferably the cancer is mesothelioma, testicular cancer or pancreatic cancer.

The peptide of the invention will generally be used in an amount to achieve the intended purpose. For use to treat or prevent a cancer, the peptide or the pharmaceutical compositions thereof, is administered or applied in a therapeutically effective amount. A "therapeutically effective amount" is an amount effective to ameliorate or prevent the symptoms, or prolong the survival of the subject being treated. Determination of a therapeutically effective amount is well within the capabilities of those skilled in the art, especially in light of the detailed disclosure provided herein.

For systemic administration, a therapeutically effective amount or dose can be estimated initially from in vitro assays. For example, a dose can be formulated in animal models to achieve a circulating concentration range that includes the IC50 as determined in cell culture. Such information can be used to more accurately determine useful doses in humans.

Initial doses can also be estimated from in vivo data, e.g. animal models, using techniques that are well known in the art. One ordinarily skill in the art could readily optimise administration to humans based on animal data and will, of course, depend on the subject being treated, on the subject's weight, the severity of the disorder, the manner of administration and the judgement of the prescribing physician.

The present disclosure also provides a method of treating or preventing cancer in a subject in need thereof, comprising administering to said subject a therapeutically effective amount of the pharmaceutical composition as described herein.

Examples of cancers, which can be treated or prevented, have been described above. Preferably, the cancer is mesothelioma, testicular cancer or pancreatic cancer.

In preferred methods, the subject is a human patient, and the administered peptide which enhances selectively the ability of at least one drug to kill cancer cells is the TAT-RasGAP$_{317-326}$ peptide.

Embraced by the scope of the present invention is also a method for enhancing apoptosis selectively in a cancer cell, comprising contacting a cancer cell with at least one peptide of the present invention and a drug.

Also envisioned is a method for selectively killing cancer cells comprising contacting a cancer cell with at least one peptide of the present invention and a drug.

The use of the peptide disclosed herein for enhancing the ability of a drug to kill cells selectively in cancer cells is also envisioned.

A further object of the present invention is to provide a kit for treating or preventing cancer in a subject, said kit comprising at least one peptide as described herein optionally with reagents and/or instructions for use.

Generally, the kit comprises a container and a label or package insert on or associated with the container. Suitable containers include, for example, bottles, vials, syringes, etc. The containers may be formed from a variety of materials such as glass or plastic. The container holds a composition which is effective for treating the cancer and may have a sterile access port (for example the container may be an intravenous solution bag or a vial having a stopper pierceable by a hypodermic injection needle). The label or package insert indicates that the composition is used for treating the cancer of choice.

Optionally, the kit further comprises a separate pharmaceutical dosage form comprising an additional anti-cancer agent selected from the group consisting of drugs as described above, anti-epidermal growth factor receptors antibodies, radioimmunotherapeutic agents, and combinations thereof.

EXAMPLES

Example 1

Cells and Transfection

HeLa and MCF-7 cells were maintained in RPMI 1640 (Sigma; cat. no 8758) containing 10% newborn calf serum (Sigma; cat. no N4637) at 37° C. and 5% $CO_2$. U2OS cells were maintained in DMEM (Sigma; cat. no 5796) containing 15% foetal calf serum (Sigma; cat. no F7524) at 37° C. and 5% $CO_2$. H-Meso-1 cells were maintained in RPMN 1640 containing 10% foetal calf serum at 37° C. and 5% $CO_2$. HUV-EC-C cells were maintained in human endothelial SFM medium (Gibco; cat. no 11111-044) complemented with 10% foetal calf serum, 20 ng/ml of basic fibroblast growth factor (Gibco; cat. no 13256-029), 10 ng/ml of epidermal growth factor (Gibco; cat. no 13247-051), 10 µg/ml of fibronectin (Gibco; cat. no 33016-015) at 37° C. and 5% $CO_2$. HaCat cells were maintained in keratinocyte SFM medium containing epidermal growth factor 1-53 and extract from bovine pituitary gland (Gibco; cat. no 17005-075) at 37° C. and 5% $CO_2$. HeLa cells were transfected as described previously (Yang J.-Y. and Widmann C., Mol. Cell. Biol., 21, 5346, 2001). Genotoxin treatment was performed in 6-well plates. The cells were split the day before the treatment at a concentration of $2.5 \times 10^5$ cells/well. U2OS cells were transfected in 6 well plates using the calcium/phosphate precipitation procedure (Jordan M. et al, "Transfecting mammalian cells: optimization of critical parameters affecting calcium-phosphate precipitate formation" Nucleic Acids Res., 24, 596, 1996). Briefly, plasmids were diluted in 90 μl H$_2$O, mixed with 10 μl CaCl$_2$ 2.5 M and incubated 10 min at room temperature. Then, 100 μl of HEP solution (280 mM NaCl, 10 mM KCl, 1.5 mM Na$_2$HPO$_4$, 12 mM D-glucose, 50 mM HEPES) was rapidly mixed with the DNA solution, incubated at room temperature for exactly 1 min, and finally transferred to the cell culture medium. After 8 hours at 37° C. and 5% CO$_2$, the medium was replaced with fresh culture medium and the cells were further incubated for 16-24 hours before being analyzed.

Chemicals.

Cisplatin and mitoxantrone were from Sigma (cat. no P4394 and no M6545, respectively). Cisplatin was diluted in DMSO at a final concentration of 100 mM and stored at −20° C. Mitoxantrone was diluted in ethanol 100% at a final concentration of 10 mM and stored at −80° C. Adriamycin was from Calbiochem (cat. no 324380). It was diluted in water at a final concentration of 10 mM and stored at −20° C. Hoechst 33342 was from Roche (cat. no H-1399). It was diluted in water at a final concentration of 10 mg/ml and stored at 4° C. in the dark.

Peptide Synthesis and Labeling.

The HIV-TAT$_{48-57}$ (GRKKRRQRRR) (SEQ ID NO: 15) and TAT-RasGAP$_{317-326}$ (GRKKRRQRRRGGWMWVT-NLRTD) (SEQ ID NO: 16) peptides were synthesized at the Institute of Biochemistry, University of Lausanne, Switzerland using FMOC technology, purified by HPLC and tested by mass spectrometry.

Fluorescein isothiocyanate (FITC)-labeling was performed on the sequence β-alanine-GRKKRRQRRRGGWM-WVTNLRTD (SEQ ID NO: 16) whose side chain Fmoc-protected amino acids were Arg(bpf), Lys(Boc), Gln(Trt), Trp(Boc), Thr(tBu), Asn(Trt), and Asp(OtBu). The peptide was synthesized stepwise on 0.2 mmol Rink Amide AM resin using Fmoc chemistry. The synthesis was monitored by ninhydrin test. After the coupling of β-alanine, the Fmoc group was removed with 20% piperidine in dimethylformamide (DMF). At this stage, a fluorescein group was conjugated to the N-terminus of peptide with FITC (5 fold excess over the substitution of the resin in 4 ml DMF and 1 ml N-ethyldiisopropylamine) to form the fluorescein-derivated peptide.

Peptides were dissolved in deionised water at a final concentration of 1 mM and stored at −20° C. until further use.

Plasmids.

The extension dn3 in the name of a plasmid indicates that the backbone plasmid is the expression vector pcDNA3 (Invitrogen). All the constructs were tagged with the HA sequence (MGYPYDVPDYAS) (SEQ ID NO: 17) at the N amino-terminal end. Plasmid N2.dn3 encodes the human RasGAP fragment N2, plasmids SH2-SH3.dn3 encodes human RasGAP amino acids 158-361, plasmids SH2.dn3 encodes human RasGAP amino acids 158-277, plasmids SH3.dn3 encodes human RasGAP amino acids 279-361. Plasmids IκBαΔN2 encodes a form of IκBα that blocks the activation of NFκB (Yang and Widmann, 2002b). Plasmid pEGFP-C1, encoding the GFP protein, was from Clontech. pRL-TK, a vector encoding the *Renilla reniformis* luciferase, was from Promega. prLUC is a reporter plasmid bearing the firefly luciferase cDNA under the control of NFκB-responsive elements (Yang J.-Y. and Widmann C., Mol. Cell. Biol., 21, 5346, 2001).

Apoptosis Measurements.

Apoptosis was determined by scoring the number of cells displaying pycnotic nuclei. Nuclei of live cells were labeled with Hoechst 33342 (10 μg/ml final concentration) for about 5 minutes and the cells were then analyzed (at least 400 cells per condition) using an inverted Leica DMIRB microscope equipped with fluorescence and transmitted light optics. Assessment of apoptosis was performed one day after the transfection or treatment of the cells. In experiment involving transfected cells, pEGFP-C1 was included in the transfection solution to label the transfected cells with GFP. In this case, the extent of apoptosis was assessed in the transfected cells only.

Luciferase Reporter Assay.

Luciferase assay was performed using the Dual-Luciferase® Reporter Assay from Promega (cat. no E1910). The cells were lysed from a 6 wells-plate using 100 μl of PLB lysis buffer provided from the Promega's kit and incubated thirty minutes on ice The lysate was then cleared by centrifugation at 16'000 g for 15 min. The firefly luciferase activity was recorded by mixing 20 μl of the lysate with 25 μl of the LARII Reagent and the *Renilla* luciferase activity was recorded by adding to the previous mix 25 μl of the Stop & Glo Reagent. For each measurement, light emission was quantified during 12 seconds using a Lumat LB 9501 luminometer (Berthold Technologies, Zurich, Switzerland).

Western Blot Analysis

Cells were lysed in lysis buffer (25 mM Hepes, 300 mM NaCl, 1.5 mM MgCl$_2$, 0.2 mM EDTA, 0.1 mM Na$_3$VO$_4$, 1% Triton X100, Complete EDTA-free Protease inhibitor Cocktail Tablets (Roche; cat. no 1873580). Proteins were separated on SDS-PAGE and blotted onto nitrocellulose membranes (BioRad; cat. no 162-0115). Thereafter, membranes were blocked with TBS (18 mM HCl, 130 mM NaCl, 20 mM Tris), 5% non-fat dry milk for 30 min at room temperature and incubated overnight with the appropriate primary antibody. These antibodies were detected by Alexa Fluor 680 conjugated secondary antibodies (Molecular Probes; cat. no A21109) diluted 1:2500 in TBS, 5% non-fat dry milk and subsequently visualized with the Odyssey infrared imaging system (Licor, Homburg, Germany). The primary antibody against phospho-p38 (Cell Signaling Technology; cat no 9211L) was diluted 1:500 in 5% BSA in TBS. The primary antibody against phospho-JNK (Cell Signaling Technology; cat n9551L) was diluted 1:1000 in TBS, 5% BSA. Quantitation was performed using the Odyssey infrared imaging software.

Statistical Analysis

All the statistical analyses were performed with Microsoft Excel (XP edition) using the student t-test.

Example 2

RasGAP Fragment N2 Potentiates the Apoptotic Response Induced by a Variety of Genotoxins Applicants have recently shown that fragment N2 enhances the ability of cisplatin to kill the HeLa tumor cell line (Yang J.-Y. and Widmann C., Mol. Cell. Biol., 21, 5346, 2001). To assess whether fragment N2 could potentiate the apoptotic response induced by other genotoxins, HeLa cells, expressing or not fragment N2, were subjected to increasing concentrations of adriamycin and mitoxantrone (and cisplatin as control). FIG. 1 shows that the presence of fragment N2 rendered HeLa cells at least 10 times more sensitive than control cells towards the various drugs. This result indicates that fragment N2 is a broad spectrum genotoxin sensitizor.

Identification of a Minimal Sequence within Fragment N which Enhances the Ability of a Drug to Kill Cancer Cells.

Fragment N2 is a 36 kDa protein, which can make it difficult to synthesize chemically. Characterization of a shorter sequence that would still bear the genotoxin-sensitizing ability is a critical step in the process of developing a therapeutical tool from fragment N2. In order to assess whether such a short sequence could be isolated, we generated a series of truncated version of fragment N2 (FIG. 2A) and determined their ability to potentiate cisplatin-induced apoptosis in HeLa cells (FIG. 2B). Fragment N2 contains two SH2 domains and one SH3 domain (FIG. 2A). We first determined which of these domains contained the pro-apoptotic activity of fragment N2. HeLa cells were transfected with the plasmids encoding the various SH domains, in the presence or in the absence of 0.15 μM cisplatin, a concentration at which the difference in sensitivity towards the drug between cells expressing or not fragment N2 is maximal (see FIG. 1). An empty construct or a construct encoding the SH2 domain did not enhance the ability of cisplatin to kill HeLa cells transfected with these constructs. In contrast, constructs containing the SH3 domain enhance the ability of cisplatin to kill cells vi apoptosis (FIG. 2B). The inability of the SH2 domain alone to potentiate the cell death in HeLa cells was not a consequence of reduced protein expression because Western blot analysis revealed that the SH2 domain was expressed as efficiently as the other constructs (data not shown).

Applicants next generated progressive truncations in the SH3 domain in an attempt to identify a minimal genotoxin-sensitizing sequence. All these constructs (see FIG. 2A), including the shortest one (317-326) that codes for a 10 amino acid long peptide, potentiated the ability of cisplatin to kill HeLa cells (FIG. 2B). These results suggest that the cell-death sensitizing property of fragment N2 does not require a complete SH domain but is mediated by a very short peptidic sequence.

The HIV-$TAT_{48-57}$Peptide Conjugated with the 317-326 Rasgap Sequence Acts as Cell Permeable Genotoxin-Sensitizing Peptide.

If a plasmid encoding amino acid 317-326 of RasGAP has the ability to enhance the ability of a drug to kill cancer cells, a synthetic peptide corresponding to the 316-326 should also display this activity provided that it can penetrate cells. It has been demonstrated that the addition of a short sequence derived from the HIV TAT protein (HIV-$TAT_{45-57}$) allows polypeptides to accumulate efficiently in cells (Schwarze S. R. et al., "In vivo protein transduction: delivery of abiologically active protein into the mouse" Science, 285, 1569, 1999). Applicants therefore synthesized apeptide containing the amino acids 317-326 of RasGAP covalently bound to the amino acids carrier peptide HV-$TAT_{48-57}$. Two glycine residues were inserted between the TAT and RasGAP sequences as spacer to allow flexibility. As a mean to assess the cellular uptake of this peptide (thereafter called TAT-$RasGAP_{317-326}$ peptide), we labeled it with the FITC fluorophore. The labeled peptide was incubated with four different tumor cell lines: a human adenocarcinoma from cervix (HeLa cells), a human osteosarcoma (U2OS cells), a breast cancer cell line (MCF-7 cells) and a human malignant mesothelomia (H-Meso-1 cells) and two non cancer cell lines (HaCat human skin keratinocyte cell line and the HUV-EC-C human umbilical endothelial cells). As shown in FIG. 3, the TAT-$RasGAP_{317-326}$ peptide efficiently entered all these cell lines. No difference in translocation of the peptide was noted between the non cancer cells and the cancer cells. We first assessed the sensitivity of the cancer cell lines towards increasing concentrations of the three genotoxins (data not shown). This allowed us to determine the sub-lethal concentrations of the genotoxins for each cell lines tested. Surprisingly, Applicants have shown that the TAT-$RasGAP_{317-326}$ peptide, but not the control HIV-$TAT_{48-57}$ peptide lacking the RasGAP sequences, enhanced the ability of cisplatin, adriamycin, and mitoxantrone to kill the tested cancer cell lines and that did not, or only marginally, induce apoptosis in control conditions. In contrast, the apoptotic response induced by cisplatin, adriamycin and mitoxantrone in the two non cancer lines was unaffected by the presence of the peptides (FIG. 4B). We have therefore identified a minimal synthetic peptide able to specifically enter and enhance the ability of the drugs to kill cancer cells.

NFkB and the SAPK Pathways are not Involved in the Properties of Tat-$RasGAP_{317-326}$.

As a Ras modulator, RasGAP could affect some of the Ras-dependent pathways controlling cell death, such as the Ras-PI3K-Akt-NFkB pathway (Datta S. R. et al., "Cellular survival: a play in three Akts" Genes Dev., 13, 2905, 1999). We therefore assessed whether modulation of NFkB activity participate in the enhancing ability mediated by TAT-$RasGAP_{317-326}$. As shown in FIG. 5A, NFkB was activated in U2OS cells after a treatment with cisplatin or with TAT-$RasGAP_{317-326}$, but not upon stimulation with the control peptide HWV-$TAT_{48-57}$. Incubation of the cells with both cisplatin and TAT-$RasGAP_{317-326}$ resulted in additive activation of NFkB (FIG. 5A). The NFkB pathway participates in the induction of cell survival responses, in many cell types (Van Antwerp D. J. et al., "Suppression of TNF-alpha-induced apoptosis by NF-kappaB" Science, 274, 787, 1996; Beg A. A. and Baltimore D., "An essential role for NF-kappaB in preventing TNF-alpha-induced cell death" Science, 274, 782, 1996) but can also be required for the induction of apoptotic responses in some situations (Ryan K. M. et al., "Role of NF-kappaB in p53-mediated programmed cell death" Nature, 404, 892, 2000). To determine whether activation of NFkB by TAT-$RasGAP_{317-326}$ was required for the enhancing ability function, a non-degradable form of IkB (IkBαΔN2) was expressed in cells. As expected, this construct efficiently prevented the activation of NFkB by cisplatin and TAT-$RasGAP_{317-326}$ (FIG. 5B). IkBαΔN2 slightly increased the apoptotic response mediated by cisplatin (FIG. 5C). The potency of TAT-$RasGAP_{317-326}$ to enhancing ability of cisplatin to kill U2OS cells via apoptosis was however unaffected by the NFkB inhibitor (FIG. 5C). These results indicate that activation of the NFkB pathway is not involved in the cell death enhancing ability effect mediated by TAT-$RasGAP_{317-326}$.

The stress-activated protein kinases (SAPKs)—the JNKs and the p38 MAPKs—have been implicated in the apoptotic response induced by various stimuli (Jarpe M. B. et al., Oncogene, 17, 1475, 1998). FIG. 6 shows that neither the control HIV-$TAT_{48-57}$ peptide nor the TAT-$RasGAP_{317-326}$ peptide activated these MAPK pathways. These peptides were also not able to increase the ability of cisplatin to stimulate the JNK or the p38 MAPKs (FIG. 6). These results indicate that the stress-activated MAPK pathways are not implicated in the capacity of TAT-$RasGAP_{317-326}$ to enhance the ability of genotoxins to kill cancer cells.

The invention claimed is:

1. A pharmaceutical composition comprising
   i) at least one peptide fragment of the N2 sequence of the RasGAP protein which comprises the amino acid sequence WXWVTXXRTX (SEQ ID NO:14), wherein said at least one peptide fragment is less than 90% of the length of said N2 sequence, and wherein X represents an amino acid, or a retro-inverso form of said at least one peptide fragment, and ii) a genotoxin, wherein said at least one peptide fragment or the retro-inverso form thereof enhances the ability of said genotoxin to kill selectively cancer cells.

2. The pharmaceutical composition of claim 1, wherein said at least one peptide fragment comprises at least one amino acid sequence encoded by a nucleotide sequences selected from the group consisting of SEQ ID NO:1, SEQ ID NO:2, SEQ ID NO:3, and SEQ ID NO:4.

3. The pharmaceutical composition of claim 1, wherein said at least one peptide fragment comprises the amino acid sequence WMWVTNLRTD (SEQ ID NO: 8).

4. The pharmaceutical composition of claim 1, wherein said at least one peptide fragment further comprises at least one amino acid in D-form.

5. The pharmaceutical composition of claim 4, wherein said D-form amino acids are in retro-inverso form.

6. The pharmaceutical composition of claim 1, wherein said at least one peptide fragment is further conjugated to an agent which increases the cell accumulation of said at least one peptide fragment.

7. The pharmaceutical composition of claim 6, wherein the agent is a cell membrane permeable carrier.

8. The pharmaceutical composition of claim 7, wherein the cell membrane permeable carrier is a peptide.

9. The pharmaceutical composition of claim 8, wherein the cell membrane permeable carrier peptide comprises at least one amino acid in D-form.

10. The parmaceutical composition of claim 9, wherein said D-form amino acids are in retro-inverso form.

11. The pharmaceutical composition of claim 8, wherein the cell membrane permeable carrier peptide is an arginine rich peptide which is selected from the group consisting of an HIV-$TAT_{48-57}$ peptide (SEQ ID NO:15), an FHV-$coat_{35-49}$ peptide, an HTLV-II $Rex_{4-16}$ peptide, and a BMV $gag_{7-25}$ peptide.

12. The pharmaceutical composition of claim 8, wherein said at least one peptide fragment comprises at least one amino acid in retro-inverso form.

13. The pharmaceutical composition of claim 1, wherein the genotoxin is selected from the group consisting of an alkylating agent, an antimetabolite, a DNA cutter, a DNA binder, a topoisomerase poison, and a spindle poison.

14. The pharmaceutical composition of claim 13, wherein said alkylating agent is selected from the group consisting of lomustine, carmustine, streptozocin, mechlorethamine, melphalan, uracil nitrogen mustard, chlorambucil, cyclosphamide, iphosphamide, cisplatin, carboplatin, mitomycin, thiotepa, dacarbazin, procarbazine, hexamethyl melamine, triethylene melamine, busulfan, pipobroman, mitotane, and other platinum compounds.

15. The pharmaceutical composition of claim 1, wherein said at least one peptide fragment comprises the SH3 domain of the N2 sequence, or a part thereof.

16. The pharmaceutical composition of claim 1, wherein said at least one peptide fragment comprises at least one amino acid in retro-inverso form.

17. The pharmaceutical composition of claim 1, wherein said at least one peptide fragment is less than 60% of the length of said N2 sequence.

18. The pharmaceutical composition of claim 1, wherein said at least one peptide fragment is less than 30% of the length of said N2 sequence.

19. A method for enhancing apoptosis selectively in a cancer cell, comprising contacting a cancer cell with a therapeutically effective amount of the pharmaceutical composition of claim 1.

20. A method for selectively killing cancer cells comprising contacting a cancer cell with a therapeutically effective amount of the pharmaceutical composition of claim 1.

21. A pharmaceutical composition comprising
   i) at least one peptide fragment of the N2 sequence of the RasGAP protein which comprises the amino acid sequence WXWVTXXRTX (SEQ ID NO:14), wherein said at least one peptide fragment is less than 90% of the length of said N2 sequence, and wherein X represents an amino acid, or a retro-inverso form of said at least one peptide, and
   ii) a genotoxin, wherein said genotoxin is a DNA cutter,
and wherein said at least one peptide fragment or the retro-inverso form thereof enhances the ability of said genotoxin to kill selectively cancer cells.

22. The pharmaceutical composition of claim 21, wherein the DNA cutter is bleomycin.

23. A pharmaceutical composition comprising
   i) at least one peptide fragment of the N2 sequence of the RasGAP protein which comprises the amino acid sequence WXWVTXXRTX (SEQ ID NO:14), wherein said at least one peptide fragment is less than 90% of the length of said N2 sequence, and wherein X represents an amino acid, or a retro-inverso form of said at least one peptide, and
   ii) a genotoxin, wherein said genotoxin is a topoisomerase poison,
and wherein said at least one peptide fragment or the retro-inverso form therof enhances the ability of said genotoxin to kill selectively cancer cells.

24. The pharmaceutical composition of claim 23, wherein the toposiomerase poison is selected from the group consisting of topotecan, irinotecan, camptothecin sodium salt, daorubicin, doxorubicin, idarubicin, mitoxantrone, teniposide, adriamycin, and etoposide.

25. A pharmaceutical composition comprising
   i) at least one peptide fragment of the N2 sequence of the RasGAP protein which comprises the amino acid sequence WXWVTXXRTX (SEQ ID NO: 14), wherein said at least one peptide fragment is less than 90% of the length of said N2 sequence, and wherein X represents an amino acid, or a retro-inverso form of said at least one peptide, and
   ii) a genotoxin, wherein said genotoxin is a DNA binder,
and wherein said at least one peptide fragment or the retro-inverso form thereof enhances the ability of said genotoxin to kill selectively cancer cells.

26. The pharmaceutical composition of claim 25, wherein the DNA binder is dactinomycin or mithramycin.

27. A pharmaceutical composition comprising
   i) at least one peptide fragment of the N2 sequence of the RasGAP protein which comprises the amino acid sequence WXWVTXXRTX (SEQ ID NO:14), wherein said at least one peptide fragment is less than 90% of the length of said N2 sequence, and wherein X represents an amino acid, or a retro-inverso form of said at least one peptide, and
   ii) a genotoxin, wherein said genotoxin is a spindle poison,
and wherein said at least one peptide fragment or the retro-inverso form thereof enhances the ability of said genotoxin to kill selectively cancer cells.

28. The pharmaceutical composition of claim 27, wherein the spindle poison is selected from the group consisting of vinblastin, vincristin, navelbin, paclitaxel, and docetaxel.

29. A pharmaceutical composition comprising
   i) at least one peptide fragment of the N2 sequence of the RasGAP protein which comprises the amino acid sequence WXWVTXXRTX (SEQ ID NO: 14), wherein said at least one peptide fragment is less than 90% of the length of said N2 sequence, and wherein X represents an amino acid, or a retro-inverso form of said at least one peptide, and
   ii) a genotoxin, wherein said genotoxin is an antimetabolite,
and wherein said at least one peptide fragment or the retro-inverso form thereof enhances the ability of said genotoxin to kill selectively cancer cells.

30. The pharmaceutical composition of claim 29, wherein the antimetabolite is selected from the group consisting of methotrexate, trimetrexate, pentostatin, cytarabin, ara-CMP, fludarabine phosphate, hydroxyurea, fluorouracyl, floxuridine, chlorodeoxyadenosine, gemcitabine, thioguanine, and 6-mercaptopurine.

31. A kit for treating cancer in a subject comprising a pharmaceutical composition comprising
   i) at least one peptide fragment of the N2 sequence of the RasGAP protein which comprises the amino acid sequence WXWVTXXRTX (SEQ ID NO:14), wherein X represents an amino acid, or a retro-inverso form of said at least one peptide fragment, and
   ii) a genotoxin,
wherein said at least one peptide fragment or the retro-inverso form thereof enhances the ability of said genotoxin to kill selectively cancer cells, and instructions for use.

32. The kit of claim 31, further comprising a separate pharmaceutical dosage form including an additional anti-cancer agent selected from the group consisting of drugs, anti-epidermal growth factor receptors antibodies, radioimmunotherapeutic agents, and combinations thereof.

33. The kit of claim 31, wherein said at least one peptide fragment is less than 90% of the length of said N2 sequence.

34. The kit of claim 31, wherein said at least one peptide fragment is less than 60% of the length of said N2 sequence.

35. The kit of claim 31, wherein said at least one peptide fragment is less than 30% of the length of said N2 sequence.

36. A kit for treating cancer in a subject comprising
   i) at least one peptide fragment of the N2 sequence of the RasGAP protein which comprises the amino acid sequence WXWVTXXRTX (SEQ ID NO:14), wherein X represents an amino acid; or a retro-inverso form of said at least one peptide fragment, and
   ii) a genotoxin,
wherein said at least one peptide fragment or the retro-inverso form thereof enhances the ability of said genotoxin to kill selectively cancer cells, and instructions for use of said at least one peptide fragment or the retro-inverso form thereof and the genotoxin.

37. The kit of claim 36, wherein said at least one peptide fragment is less than 90% of the length of said N2 sequence.

38. The kit of claim 36, wherein said at least one peptide fragment is less than 60% of the length of said N2 sequence.

39. The kit of claim 36, wherein said at least one peptide fragment is less than 30% of the length of said N2 sequence.

40. A method for enhancing apoptosis in a cancer cell, comprising contacting the cancer cell with a therapeutically effective amount of
   i) at least one peptide fragment of the N2 sequence of the RasGAP protein which comprises the amino acid sequence WXWVTXXRTX (SEQ ID NO:14), wherein said at least one peptide fragment is less than 90% of the length of said N2 sequence, and wherein X represents an amino acid, or a retro-inverso form of said at least one peptide fragment, and ii) a genotoxin, wherein said at least one peptide fragment or the retro-inverso form thereof enhances the ability of said genotoxin to selectively kill said cancer cell.

41. The method of claim 40, wherein said at least one peptide fragment comprises the SH3 domain of the N2 sequence, or a part thereof, or comprises at least one amino acid sequence encoded by a nucleotide sequence selected from the group consisting of SEQ ID NO:1, SEQ ID NO:2, SEQ ID NO:3, and SEQ ID NO:4.

42. The method of claim 40, wherein the genotoxin is selected from the group consisting of an alkylating agent, an antimetabolite, a DNA cutter, a DNA binder, a topoisomerase poison, and a spindle poison.

43. The method of claim 40, wherein the genotoxin is selected from the group consisting of cisplatin, mitoxantrone and adriamycin.

44. The method of claim 40, wherein said at least one peptide fragment is less than 60% of the length of said N2 sequence.

45. The method of claim 40, wherein said at least one peptide fragment is less than 30% of the length of said N2 sequence.

46. A method for enhancing the sensitivity of a cancer cell to a genotoxin comprising contacting the cancer cell with a genotoxin and a therapeutically effective amount of at least one peptide fragment of the N2 sequence of the RasGAP protein which comprises the amino acid sequence WXWVTXXRTX (SEQ ID NO: 14), wherein said at least one peptide fragment is less than 90% of the length of said N2 sequence, and wherein X represents an amino acid, or a retro-inverso form of said at least one peptide, thereby enhancing the sensitivity of a cancer cell to the genotoxin.

47. The method of claim 46, wherein said at least one peptide fragment comprises the SH3 domain of the N2 sequence, or a part thereof, or comprises at least one amino acid sequence encoded by a nucleotide sequence selected from the group consisting of SEQ ID NO:1, SEQ ID NO:2, SEQ ID NO:3, and SEQ ID NO:4.

48. A method of treating cancer in a subject comprising administering to said subject a therapeutically effective amount of i) at least one peptide fragment of the N2 sequence of the RasGAP protein which comprises the amino acid sequence WXWVTXXRTX (SEQ ID NO: 14), wherein X represents an amino acid, or a retro-inverso form of said at least one peptide, and ii) a genotoxin, wherein said at least one peptide fragment or the retro-inverso form thereof enhances the ability of said genotoxin to kill selectively cancer cells, such that said cancer is treated.

49. The method according to claim 48, wherein the cancer is selected from the group consisting of carcinoma, lymphoma, blastoma, sarcoma, liposarcoma, neuroendocrine tumor, mesothelioma, schwanoma, meningioma, adenocarcinoma, melanoma, leukemia, lymphoid malignancy, squamous cell cancer, epithelial squamous cell cancer, lung cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, a tumor of the biliary tract, and head and neck cancer.

50. The method of claim 48, wherein said at least one peptide fragment comprises the SH3 domain of the N2 sequence, or a part thereof, or comprises at least one amino acid sequence encoded by a nucleotide sequence selected from the group consisting of SEQ ID NO:1, SEQ ID NO:2, SEQ ID NO:3, and SEQ ID NO:4.

51. The method of claim 48, wherein the genotoxin is selected from the group consisting of an alkylating agent, an antimetabolite, a DNA cutter, a DNA binder, a topoisomerase poison, and a spindle poison.

52. The method of claim 48, wherein the genotoxin is selected from the group consisting of cisplatin, mitoxantrone and adriamycin.

53. The method of claim 48, wherein said at least one peptide fragment is less than 90% of the length of said N2 sequence.

54. The method of claim 48, wherein said at least one peptide fragment is less than 60% of the length of said N2 sequence.

55. The method of claim 48, wherein said at least one peptide fragment is less than 30% of the length of said N2 sequence.

* * * * *

SEQUENCE LISTING

<160> NUMBER OF SEQ ID NOS: 17

<210> SEQ ID NO 1
<211> LENGTH: 249
<212> TYPE: DNA
<213> ORGANISM: Homo sapiens

<400> SEQUENCE: 1

```
gaagatagaa ggcgtgtacg agctattcta ccttacacaa aagtaccaga cactgatgaa    60
ataagttttct taaaaggaga tatgttcatt gttcataatg aattagaaga tggatggatg   120
tgggttacaa atttaagaac agatgaacaa ggccttattg ttgaagacct agtagaagag   180
gtgggccggg aagaagatcc acatgaagga aaaatatggt tccatgggaa gatttccaaa   240
caggaagct                                                            249
```

<210> SEQ ID NO 2
<211> LENGTH: 204
<212> TYPE: DNA
<213> ORGANISM: Homo sapiens

<400> SEQUENCE: 2

```
gtacgagcta ttctacctta cacaaaagta ccagacactg atgaaataag tttcttaaaa    60
ggagatatgt tcattgttca taatgaatta gaagatggat ggatgtgggt tacaaattta   120
agaacagatg aacaaggcct tattgttgaa gacctagtag aagaggtggg ccggaagaa    180
gatccacatg aaggaaaaat atgg                                           204
```

<210> SEQ ID NO 3
<211> LENGTH: 174
<212> TYPE: DNA
<213> ORGANISM: Homo sapiens

<400> SEQUENCE: 3

```
gtacgagcta ttctacctta cacaaaagta ccagacactg atgaaataag tttcttaaaa    60
ggagatatgt tcattgttca taatgaatta gaagatggat ggatgtgggt tacaaattta   120
agaacagatg aacaaggcct tattgttgaa gacctagtag aagaggtggg ccgg          174
```

<210> SEQ ID NO 4
<211> LENGTH: 30
<212> TYPE: DNA
<213> ORGANISM: Homo sapiens

<400> SEQUENCE: 4

```
tggatgtggg ttacaaattt aagaacagat                                      30
```

<210> SEQ ID NO 5
<211> LENGTH: 83
<212> TYPE: PRT
<213> ORGANISM: Homo sapiens

<400> SEQUENCE: 5

```
Glu Asp Arg Arg Arg Val Arg Ala Ile Leu Pro Tyr Thr Lys Val Pro
1               5                   10                  15
Asp Thr Asp Glu Ile Ser Phe Leu Lys Gly Met Phe Ile Val His
                20                  25                  30
Asn Glu Leu Glu Asp Gly Trp Met Trp Val Thr Asn Leu Arg Thr Asp
            35                  40                  45
Glu Gln Gly Leu Ile Val Glu Asp Leu Val Glu Glu Val Gly Arg Glu
```

```
                        50                  55                  60
Glu Asp Pro His Glu Gly Lys Ile Trp Phe His Gly Lys Ile Ser Lys
 65                  70                  75                  80

Gln Glu Ala

<210> SEQ ID NO 6
<211> LENGTH: 69
<212> TYPE: PRT
<213> ORGANISM: Homo sapiens

<400> SEQUENCE: 6

Arg Val Arg Ala Ile Leu Pro Tyr Thr Lys Val Pro Asp Thr Asp Glu
  1               5                  10                  15

Ile Ser Phe Leu Lys Gly Asp Met Phe Ile Val His Asn Glu Leu Glu
                 20                  25                  30

Asp Gly Trp Met Trp Val Thr Asn Leu Arg Thr Asp Glu Gln Gly Leu
             35                  40                  45

Ile Val Glu Asp Leu Val Glu Val Gly Arg Glu Glu Asp Pro His
         50                  55                  60

Glu Gly Lys Ile Trp
 65

<210> SEQ ID NO 7
<211> LENGTH: 59
<212> TYPE: PRT
<213> ORGANISM: Homo sapiens

<400> SEQUENCE: 7

Arg Val Arg Ala Ile Leu Pro Tyr Thr Lys Val Pro Asp Thr Asp Glu
  1               5                  10                  15

Ile Ser Phe Leu Lys Gly Asp Met Phe Ile Val His Asn Glu Leu Glu
                 20                  25                  30

Asp Gly Trp Met Trp Val Thr Asn Leu Arg Thr Asp Glu Gln Gly Leu
             35                  40                  45

Ile Val Glu Asp Leu Val Glu Val Gly Arg
         50                  55

<210> SEQ ID NO 8
<211> LENGTH: 10
<212> TYPE: PRT
<213> ORGANISM: Homo sapiens

<400> SEQUENCE: 8

Trp Met Trp Val Thr Asn Leu Arg Thr Asp
  1               5                  10

<210> SEQ ID NO 9
<211> LENGTH: 10
<212> TYPE: PRT
<213> ORGANISM: Bos taurus

<400> SEQUENCE: 9

Trp Met Trp Val Thr Asn Leu Arg Thr Asp
  1               5                  10

<210> SEQ ID NO 10
<211> LENGTH: 10
<212> TYPE: PRT
<213> ORGANISM: Mus musculus

<400> SEQUENCE: 10
```

```
Trp Met Trp Val Thr Asn Leu Arg Thr Asp
1               5                   10

<210> SEQ ID NO 11
<211> LENGTH: 10
<212> TYPE: PRT
<213> ORGANISM: Rattus norvegicus

<400> SEQUENCE: 11

Trp Met Trp Val Thr Asn Leu Arg Thr Asp
1               5                   10

<210> SEQ ID NO 12
<211> LENGTH: 10
<212> TYPE: PRT
<213> ORGANISM: Anopheles albimanus

<400> SEQUENCE: 12

Trp Leu Trp Val Thr Ala His Arg Thr Gly
1               5                   10

<210> SEQ ID NO 13
<211> LENGTH: 10
<212> TYPE: PRT
<213> ORGANISM: Drosophila melanogaster

<400> SEQUENCE: 13

Trp Leu Trp Val Thr Ala His Arg Thr Gly
1               5                   10

<210> SEQ ID NO 14
<211> LENGTH: 10
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa corresponds to an amino acid residue that
      can be cahnged by conservative or non-conservative amino-acid
      substitution.
<220> FEATURE:
<221> NAME/KEY: MISC_FEATURE
<222> LOCATION: (6)..(7)
<223> OTHER INFORMATION: Xaa correspond to amino acid residues that can
      be changed by conservative or non-conservative amino-acid
      substitutions.
<220> FEATURE:
<221> NAME/KEY: MISC_FEATURE
<222> LOCATION: (10)..(10)
<223> OTHER INFORMATION: Xaa corresponds to an amino acid residue that
      can be changed by conservative or non-conservative amino-acid
      substitution.
<220> FEATURE:
<221> NAME/KEY: MISC_FEATURE
<222> LOCATION: (10)..(10)
<223> OTHER INFORMATION: Xaa corresponds to an amino acid residue that
      can be changed by conservative or non-conservative amino-acid
      substitution.

<400> SEQUENCE: 14

Trp Xaa Trp Val Thr Xaa Xaa Arg Thr Xaa
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15
```

```
Gly Arg Lys Lys Arg Arg Gln Arg Arg Arg
1               5                   10

<210> SEQ ID NO 16
<211> LENGTH: 22
<212> TYPE: PRT
<213> ORGANISM: Artificial Sequence
<220> FEATURE:
<223> OTHER INFORMATION: Synthetic Construct

<400> SEQUENCE: 16

Gly Arg Lys Lys Arg Arg Gln Arg Arg Arg Gly Gly Trp Met Trp Val
1               5                   10                  15

Thr Asn Leu Arg Thr Asp
            20

<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

Met Gly Tyr Pro Tyr Asp Val Pro Asp Tyr Ala Ser
1               5                   10
```